(12) United States Patent
Li et al.

(10) Patent No.: US 12,202,834 B2
(45) Date of Patent: Jan. 21, 2025

(54) SOLID STATE FORMS OF OCLACITINIB MALEATE

(71) Applicant: VationPharma B.V., Panningen (NL)

(72) Inventors: Bin Li, Zhejiang (CN); Analia Ivanna Chamorro Orue, Bochum (DE); Anna Katharina Mellor, Bristol (GB)

(73) Assignee: VationPharma B.V., Panningen (NL)

( * ) Notice: Subject to any disclaimer, the term of this patent is extended or adjusted under 35 U.S.C. 154(b) by 807 days.

(21) Appl. No.: 17/426,931

(22) PCT Filed: Jan. 29, 2020

(86) PCT No.: PCT/NL2020/050045
§ 371 (c)(1),
(2) Date: Jul. 29, 2021

(87) PCT Pub. No.: WO2020/159362
PCT Pub. Date: Aug. 6, 2020

(65) Prior Publication Data
US 2022/0098206 A1   Mar. 31, 2022

(30) Foreign Application Priority Data

Jan. 29, 2019  (NL) ..................................... 2022471

(51) Int. Cl.
*C07D 487/04* (2006.01)
(52) U.S. Cl.
CPC ........ *C07D 487/04* (2013.01); *C07B 2200/13* (2013.01)
(58) Field of Classification Search
CPC .................................................. C07D 487/04
See application file for complete search history.

(56) References Cited

U.S. PATENT DOCUMENTS

| | | |
|---|---|---|
| 3,037,980 A | 6/1962 | Hitchings |
| 3,670,079 A | 6/1972 | Patanelli |
| 4,456,464 A | 6/1984 | Lee |
| 4,526,608 A | 7/1985 | Lee |
| 4,590,282 A | 5/1986 | Henrick |
| 4,879,309 A | 11/1989 | Doll |
| 4,933,339 A | 6/1990 | Sharma |
| 4,997,936 A | 3/1991 | Christensen |
| 5,134,123 A | 7/1992 | Branca |
| 5,356,903 A | 10/1994 | Eissenstat |
| 5,389,509 A | 2/1995 | Maskasky |
| 5,496,946 A | 3/1996 | Akimoto |
| 5,686,457 A | 11/1997 | Traxler |
| 6,080,747 A | 6/2000 | Uckun |
| 6,136,595 A | 10/2000 | Ihle |
| 6,180,636 B1 | 1/2001 | Traxler |
| 6,187,552 B1 | 2/2001 | Roberds |
| 6,310,063 B1 | 10/2001 | Ge |
| 6,506,762 B1 | 1/2003 | Horvath |
| 6,552,192 B1 | 4/2003 | Hanus |
| 6,635,762 B1 | 10/2003 | Blumenkopf |
| 6,890,929 B2 | 5/2005 | Blumenkopf |
| 6,965,027 B2 | 11/2005 | Flanagan |
| 7,192,963 B2 | 3/2007 | Blumenkopf |
| 7,244,729 B2 | 7/2007 | Bold |
| 7,250,420 B2 | 7/2007 | Changelian |
| 7,253,166 B2 | 8/2007 | Ding |
| 7,253,286 B2 | 8/2007 | Funahashi |
| 7,301,023 B2 | 11/2007 | Flanagan |
| 7,432,370 B2 | 10/2008 | Wilcox |
| 7,465,726 B2 | 12/2008 | Ahmed |
| 7,569,569 B2 | 8/2009 | Blumenkopf |
| 7,601,727 B2 | 10/2009 | Blumenkopf |
| 2005/0159433 A1 | 7/2005 | Changelian |
| 2005/0159434 A1 | 7/2005 | Flanagan |
| 2005/0171128 A1 | 8/2005 | Blumenkopf |
| 2006/0025383 A1 | 2/2006 | Wishart |

FOREIGN PATENT DOCUMENTS

| | | |
|---|---|---|
| CN | 1439010 A | 8/2003 |
| CN | 107365312 A | 11/2017 |
| EP | 0334636 A2 | 9/1989 |
| EP | 0682027 A1 | 11/1995 |
| EP | 0795556 A1 | 9/1997 |
| GB | 915303 A | 1/1963 |
| GB | 915304 A | 1/1963 |
| JP | 2002518393 A | 6/2002 |
| JP | 2004501922 A | 1/2004 |
| JP | 2007529421 A | 10/2007 |
| WO | WO9519774 A1 | 7/1995 |
| WO | WO9640142 A1 | 12/1996 |

(Continued)

OTHER PUBLICATIONS

International Search Report and Written Opinion, International Application No. PCT/NL2020/050045, mailed Jun. 3, 2020, 15 pages.
Mino R Caira Ed—Montchamp Jean-Luc: "Crystalline Polymorphism of Organic Compounds" Topics in Current Chemistry, Berlin, DE, vol. 198, Jan. 1, 1998, pp. 163-208.
Aaltonen J. et al: "Solid form screening—A review" European Journal of Pharmaceutics and Biopharmaceutics, Amsterdam, NL, vol. 71, No. 1, Jan. 1, 2009, pp. 23-37.
Aringer et al., "Janus kinases and theft role in growth and disease", Life Sciences, 64(24):2173-2186, 1999.
Baird et al., "T cell development and activation in Jak3-deficient mice", J. Leukocyte Biol., 63(6):669-677, 1998.
Bolen and Brugge, "Leukocyte Protein Tyrosine Kinases: Potential Targets for Drug Discovery", Annu. Rev. Immunol., 15:371-404, 1997.
Candotti et al., "Severe combined immune deficiencies due to defects of the common gamma chain-JAK3 signaling pathway", Springer Semin. Immunopathol., 19(4):401-415, 1998.

(Continued)

*Primary Examiner* — John S Kenyon
(74) *Attorney, Agent, or Firm* — Casimir Jones, S.C.; Robert A. Goetz

(57) ABSTRACT

The present invention relates to solid state forms of oclacitinib maleate and methods for the preparation of the solid state forms of oclacitinib maleate. The solid state forms of oclacitinib maleate of the present invention include amorphous oclacitinib maleate, crystalline tetramethyl urea solvate form of oclacitinib maleate, crystalline monohydrate form of oclacitinib maleate and crystalline form of oclacitinib maleate (form B).

15 Claims, 18 Drawing Sheets

(56) References Cited

FOREIGN PATENT DOCUMENTS

| | | |
|---|---|---|
| WO | WO9702262 A1 | 1/1997 |
| WO | WO9702266 A1 | 1/1997 |
| WO | WO9713771 A1 | 4/1997 |
| WO | WO9718212 A1 | 5/1997 |
| WO | WO9727199 A1 | 7/1997 |
| WO | WO9728161 A1 | 8/1997 |
| WO | WO9732879 A1 | 9/1997 |
| WO | WO9749706 A1 | 12/1997 |
| WO | WO9802437 A1 | 1/1998 |
| WO | WO9802438 A1 | 1/1998 |
| WO | WO9807726 A1 | 2/1998 |
| WO | WO9823613 A1 | 6/1998 |
| WO | WO9833798 A2 | 8/1998 |
| WO | WO9951599 A1 | 10/1999 |
| WO | WO9961428 A1 | 12/1999 |
| WO | WO9965908 A1 | 12/1999 |
| WO | WO9965909 A1 | 12/1999 |
| WO | WO0000202 A1 | 1/2000 |
| WO | WO0010981 A1 | 3/2000 |
| WO | WO0017203 A1 | 3/2000 |
| WO | WO0142246 A2 | 6/2001 |
| WO | WO0200661 A1 | 1/2002 |
| WO | WO2005020921 A2 | 3/2005 |
| WO | WO2006014325 A2 | 2/2006 |
| WO | WO2006069080 A2 | 6/2006 |
| WO | WO2006116713 A1 | 11/2006 |
| WO | WO2008089307 A2 | 7/2008 |
| WO | WO2008089310 A2 | 7/2008 |
| WO | 2010/020905 A1 | 2/2010 |
| WO | 2017/142740 A1 | 8/2017 |

OTHER PUBLICATIONS

Chen et al., "Advances in Cytokine Signaling: The Role of Jaks and STATs" Transplanaton Proc., 31(3):148-1487, 1999.
Eynon et al., "Disruption of Cytokine Signaling in Lymphoid Development: Unique Contributions of the Common Cytokine Gamma Chain and the Jak3 Kinase", J. Interferon Cytokine Res., 16(9):677-684, 1996.
Fabbro et al,, "Protein kinases as targets for anticancer agents: from inhibitors to useful drugs", Pharmacology & Therapeutics, 93:79-98, 2002.
Ghosh et al., "4-[(3-Bromo-4-hydroxyphenyl)amino]-6,7-dimethoxyquinazolin-1-ium chloride methanol solvate and 4-[(3-hydroxyphenyl)amino]-6,7-di-methoxy-1-quinazolinium chloride", Acta Cryst. SectC: Cryst. Struct. Commun., C57:76-78, 2001. Abstract provided.
Hanke et al., "Role of tyrosine kinases in lymphocyte activation: Targets for drug intervention", Inflamm, Res., 44 (9):357-371, 1995.
Ihle, "The Janus Protein Tyrosine Kinase Family and Its Role in Cytokine Signaling", Adv. Immunology, 60:1-35, 1995.
Ihle, "The Janus protein tyrosine kinases in hemoatopoietic cytokine signaling", Semin. Immunology, 7(4):247-254, 1995.
Iwamura et al., "Quantitative aspects of the receptor binding of cytokinin agonists and antagonists", J. Med. Chem., 26(6):838-844, 1983.
Johnston et al., "Phosphorylation and activation of the Jak-3 Janus kinase in response to interieukin-2", Nature, 370:151-153, 1994.
Kirken et al., "Activation of JAK3, but Not JAK1, is Critical for IL-2-Induced Proliferation and STAT5 Recruitment by a COOH-terminal Region of the IL-2 Receptor Beta-Chain", Cytokine, 7(7):689-700, 1995.
Kisseleva, "Signaling through the JAK/STAT pathway, recent advances and future challenges", Gene, 285:1-24, 2002.
Leonard and O'Shea, "JAKS and STATS: Biological Implications", Annu. Rev. Immunol., 16:293-322, 1996.
Li et al., "Blocking the Common gamma-Chain of Cytokine Receptors Induces T Cell Apoptosis and Long-Term Islet Allograft Survival", J. Immunol., 164(3):1193-1199, 2000.
Liu et al., "JAK/STAT signaling by cytokine receptors", Curr. Opin. Immunol., 10(3):271-278, 1998.

Malabarba et al., "Activation of JAK3, but Not JAK1, Is Critical to Interleukin-4 (IL4) Stimulated Proliferation and Requires a Membrane-proximal Region of IL4 Receptor alpha", J. Biol. Chem., 270:9630-9637, 1995.
Malaviya and Uckun, "Genetic and Biochemical Evidence for a Critical Role of Janus Kinase (JAK)-3 in Mast Cell-Mediated Type I Hypersensitivity Reactions", Biochem. Biophys. Res. Commun., 257(3):807-813, 1999.
Malaviya et al., "Targeting Janus Kinase 3 in Mast Cells Prevents Immediate Hypersensitivity Reactions and Anaphylaxis", J. Biol, Chem., 274(38):27028-27038, 1999.
Malaviya et al., "Treatment of Allergic Asthma by Targeting Janus Kinase 3-Dependent Leukotriene Synthesis in Mast Cells with 4-(3', 5'-Dibromo-4'-hydroxyphenyl)amino-6,7-dimethoxyquinazoline (WHI-P97)", J. Pharmacol. Exp. Ther., 295(3):912-926, 2000.
Mass, "The HER Receptor Family: A Rich Target for Therapeutic Development", Int. J. Radiation Oncology Biol. Phys., 58(3):932-940, 2004.
Moriggi et al., "Stat5 Activation is Uniquely Associated with Cytokine Signaling in Peripheral T Cells", Immunity, 11:225-230t, 1999.
Musso et al., "Regulation of JAK3 Expression in Human Monocytes: Phosphorylation in Response to Interleukins 2, 4, and 7", J. Exp. Med., 181(4):1425-1431, 1995.
Nelson et al., "Requirement for an initial signal from the membrane-proximal region of the interleukin 2 receptor gamma(c) chain for Janus kinase activation leading to T cell proliferation", Proc. Natl. Acad. Sci. USA, 94(5):1878-1883, 1997.
Notarangelo et al., "Severe Combined Immune Deficiency Due to Defects of the JAK3 Tyrosine Kinase", Progress in Immunodeficiency VI:61-68, 1996.
Oakes et al., "Signaling via IL-2 and IL-4 in JAK3-Deficient Severe Combined Immunodeficiency Lymphocytes: JAK3-Dependent and Independent Pathways", Immunity, 5(6):605-615, 1996.
Russell et al., "Interaction of IL-2Rbeta and gammac Chains with Jak1 and Jak3: Implications for XSCID and XCID", Science, 266(5187):1042-1045, 1994.
Shouda et al., "Induction of the cytokine signal regulator SOCS3/CIS3 as a therapeutic strategy for treating inflammatory arthritis", J. Clin. Invest., 108(12):1781-1786, 2001.
Simone, Cecil Textbook of Medicine, edited by Bennett, J.C., and Plum F., 20th edition, vol. 1, pp. 1004-1010, 1996.
Sudbeck and Uckun, "Recent advances in JAK3 kinase inhibitors", IDrugs, 2(10):1026-1030, 1999.
Sudbeck et al., "An inhibitor of Janus kinase 3: 4-(4-hydroxyphenlamino)-6,7-dimethoxyquinazolin-1-ium chloride methanol solvate", Acta Cryst. SectC: Cryst. Struct. Commun., C56:1282-1283, 2000.
Sudbeck et al., "Structure-based Design of Specific Inhibitors of Janus Kinase 3 as Apoptosis-including Antileukemic Agents", Clin. Cancer Res., 5(6):1569-1582, 1999.
The Medline Medical Encyclopedia entry for Psoriasis http://www.nlm.nih.gov/medlineplus/ency/article/000434.htm.
Thomas and Berg, "Peripheral Expression of Jak3 is Required to Maintain T Lymphocyte Function", J. Exp. Med., 185(2):197-206, 1997.
Thomis et al., "The Jak Family Tyrosine Kinase Jak3 is Required for IL-2 Synthesis by Naive/Resting CD4+ T Cells", J. Immunol., 163(10):5411-5417, 1999.
Traxler et al., "Protein tyrosine kinase inhibitors in cancer treatment", Exp. Opin. Ther. Patents, 7(6):571-588, 1997.
Traxler, Peter M., et al. "4-(Phenylamino) pyrrolopyrimidines: potent and selective, ATP site directed inhibitors of the EGF-receptor protein tyrosine kinase." Journal of medicinal chemistry 39.12 (1996): 2285-2292.
Trieu et al., "A Specific Inhibitor of Janus Kinase-3 Increases Survival in a Tansgenic Mouse model of Amyotrophic Lateral Sclerosis", Biochem. Biophys. Res. Commun., 267(1):22-25, 2000.
Uckun et al "In Vivo Toxicity and Pharmacokinetic Features of the Janus Kinase 3 Inhibitor WHI-P131 [4-(4'Hydoxyphenyl)-Amino-6,7-Dimethoxyquinazoline]", Clin. Cancer Res., 5(10):2954-2962, 1999.

(56) References Cited

OTHER PUBLICATIONS

Wang et al., "JAK3, STAT, and MAPK Signaling Pathways as Novel Molecular Targets for the Tyrphostin AG-490 Regulation of IL-2-Mediated T Cell Response", J. Immunol., 162(7)3897-3904, 1999.

Yamaoka, "The Janus kinases (Jaks)", Genome Biology, 5(12):253-253.6, 2004.

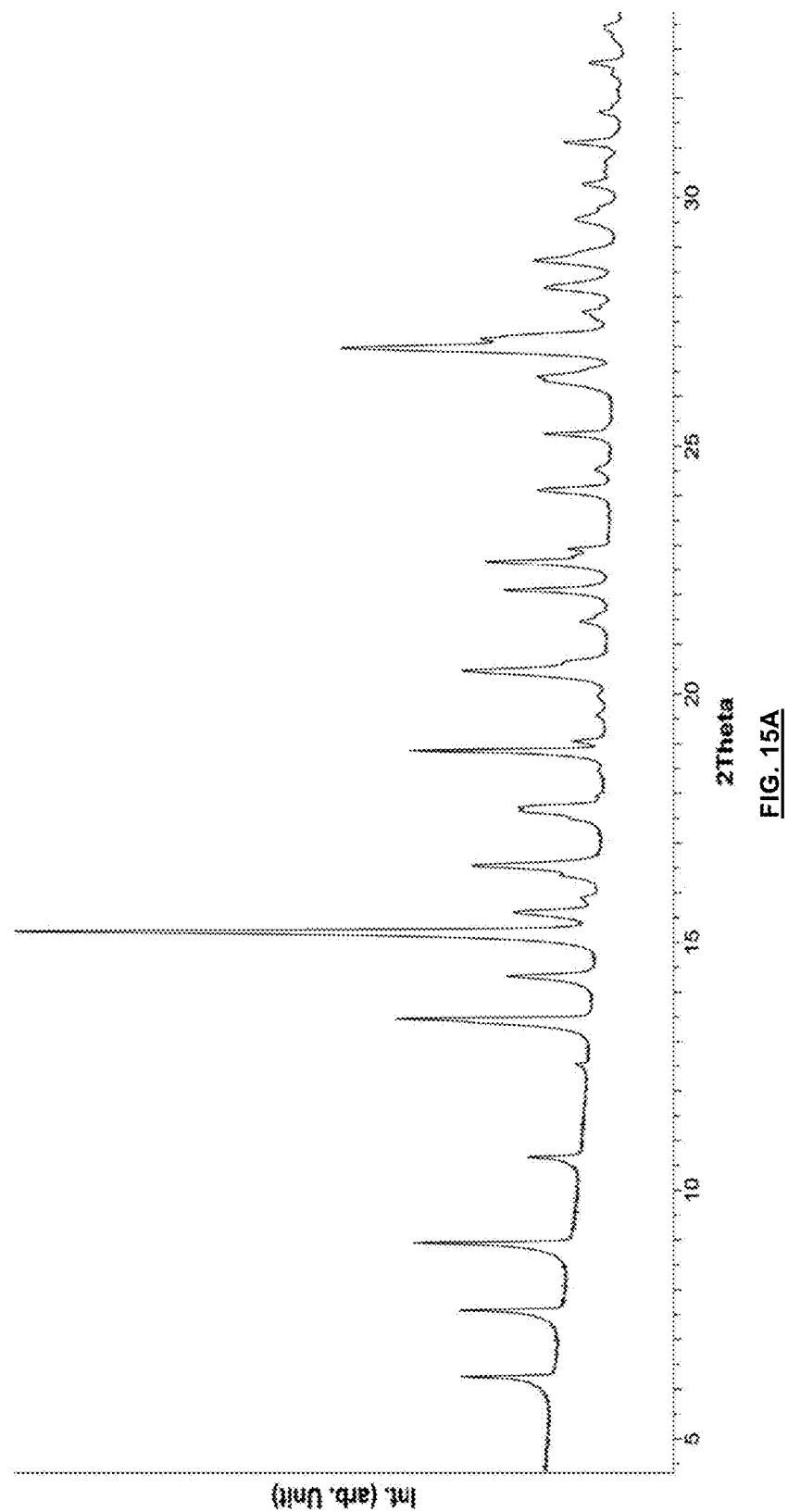

SOLID STATE FORMS OF OCLACITINIB MALEATE

The present invention relates to different solid state forms of N-methyl(4-(methyl(7H-pyrrolo[2,3-d]pyrimidin-4-yl)amino)cyclohexyl)methanesulfonamide (oclacitinib) of the following formula:

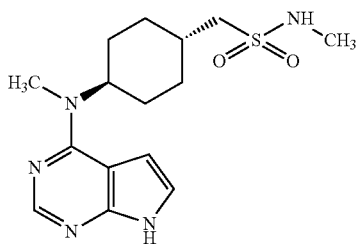 [SMILES: CNS(=O)(=O)C[C@H]1CC[C@H](N(C)c2ncnc3[nH]ccc23)CC1]

its use as Janus Kinase (JAK) inhibitor, pharmaceutical compositions comprising oclacitinib, and methods for the preparation of oclacitinib.

Protein kinases are families of enzymes that catalyse the phosphorylation of specific residues in proteins, broadly classified into tyrosine and serine/threonine kinases. Inappropriate kinase activity, arising from mutation, over-expression, or inappropriate regulation, dysregulation or deregulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

JAK inhibitors have been disclosed in International patent application published under no. WO 2010/020905 A1 describing pyrrolo[2,3-d]pyridimidine compounds, including oclacitinib, and disclosing several synthetic procedures for preparing pyrrolo[2,3-d]pyridimidine compounds, including oclacitinib.

It has been found that oclacitinib, in particular oclacitinib maleate, may exist in various solid state forms. International patent application published under no. WO 2010/020905 A1 discloses a crystalline form of N-methyl(4-(methyl(7H-pyrrolo[2,3-d]pyrimidin-4-yl)amino)cyclohexyl)methanesulfonamide maleic acid salt (oclacitinib maleate) designated as 'form A'

The ability of a substance to exist in more than one solid state form or crystalline form is defined as polymorphism and these different crystal forms are known as "polymorph modifications" or "polymorphs". Polymorphism can influence many aspects of solid state properties of a drug. Different crystal modifications of a substance may differ considerably from one another in different physical properties which may influences directly their solubility for instance. Polymorphism is found in several organic compounds.

An object of the present invention is to specifically isolate and characterize different solid state forms of oclacitinib maleate having improved properties compared to the oclacitinib maleate disclosed in the prior art and to develop processes for the preparation of oclacitinib maleate.

The object has been achieved with the identification of crystalline form oclacitinib maleate designated as 'form B', crystalline monohydrate form of oclacitinib maleate, crystalline tetramethyl urea solvate form of oclacitinib maleate and amorphous oclacitinib maleate.

Description of figures:
FIG. 15A: shows an x-ray powder diffraction pattern of crystalline form of oclacitinib maleate (form B)

The present invention relates to a crystalline form oclacitinib maleate (form B). Whereas International patent application published under no. WO 2010/020905 A1 discloses a solid state form of N-methyl(4-(methyl(7H-pyrrolo[2,3-d]

pyrimidin-4-yl)amino)cyclohexyl)methanesulfonamide maleic acid salt (oclacitinib maleate) designated as 'form A', it is now found that another crystalline form of oclacitinib maleate designated as 'form B' was identified as being non-hygroscopic. It was found that pharmaceutical compositions comprising oclacitinib maleate form B are stable and have an increased shelf-life. In comparison to oclacitinib maleate form A, it was found that the oclacitinib maleate form B is stable at conditions having a relatively high relative humidity. In fact, oclacitinib maleate form B can be stored at a relative humidity of at least 30%. It was further found that the relative humidity may be 100% without affecting the solid state of oclacitinib maleate form B providing a significant advantage compared to oclacitinib maleate form A which is only stable at relatively low relative humidity, i.e. a relative humidity of at most 30%.

The crystalline form of oclacitinib maleate (form B) as described above can further be characterized by the x-ray powder diffraction pattern as shown in FIG. 15A.

The crystalline form of oclacitinib maleate (form B) can be characterized by having an x-ray powder diffraction pattern comprising a characteristic peak at about 8.95±0.2° 2θ. The crystalline form of oclacitinib maleate (form B) can be further characterized by having an x-ray powder diffraction pattern comprising further characteristic peaks at about 7.59, 10.67, 13.47, 15.23, 20.47, 22.10, and 25.25±0.2° 2θ.

Figure 15B:
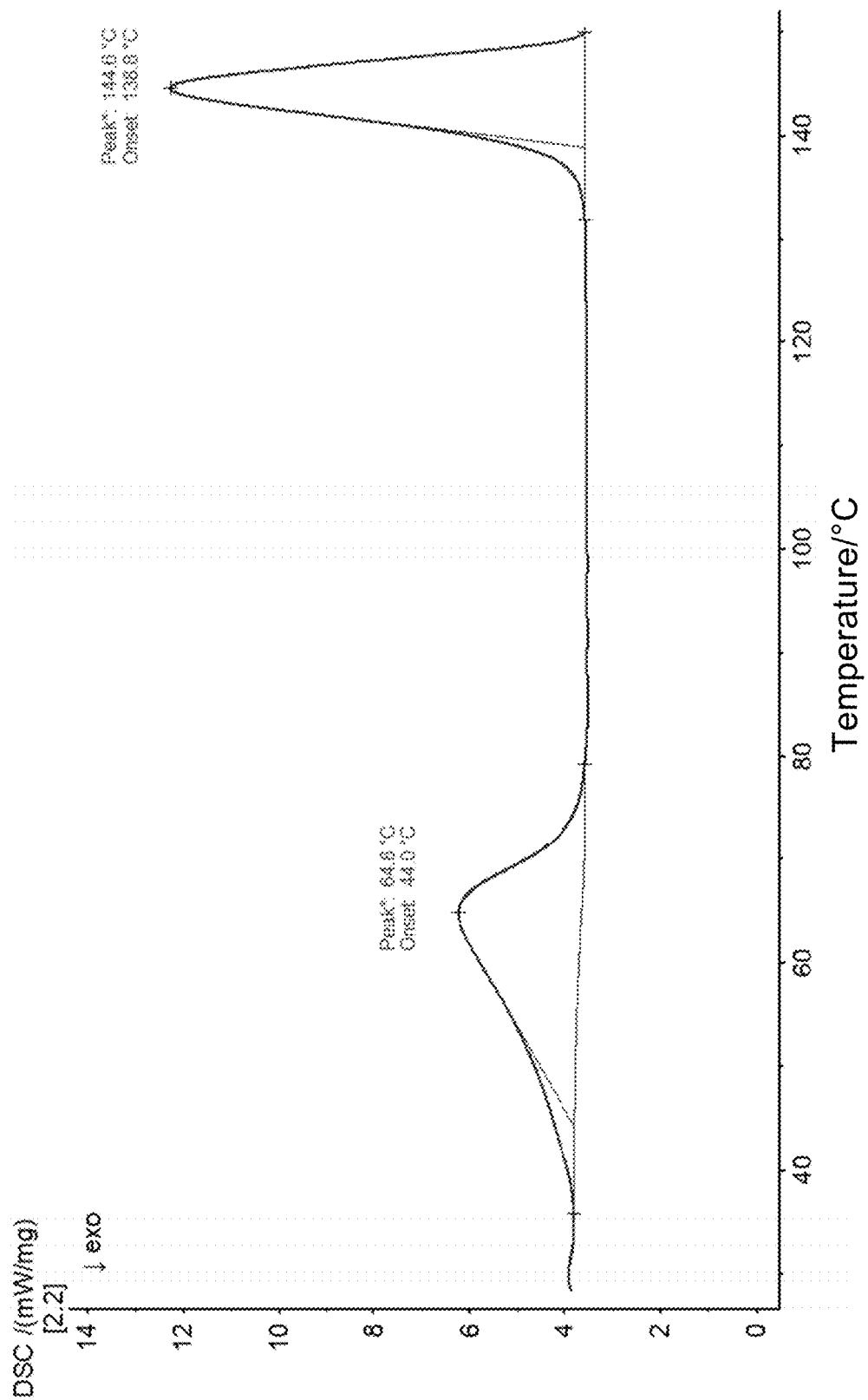
FIG. 15B: shows a DSC diagram of crystalline form of oclacitinib maleate (form B)

The crystalline form of oclacitinib maleate (form B) of the present invention can further be characterized by the DSC diagram as shown in FIG. 15B.

The crystalline form of oclacitinib maleate (form B) can be characterized by having a DSC exhibiting an endothermic peak at about 65° C. Further, the crystalline form of oclacitinib maleate (form B) can be further characterized by having a DSC further exhibiting an endothermic peak at about 145° C.

Figure 15C:
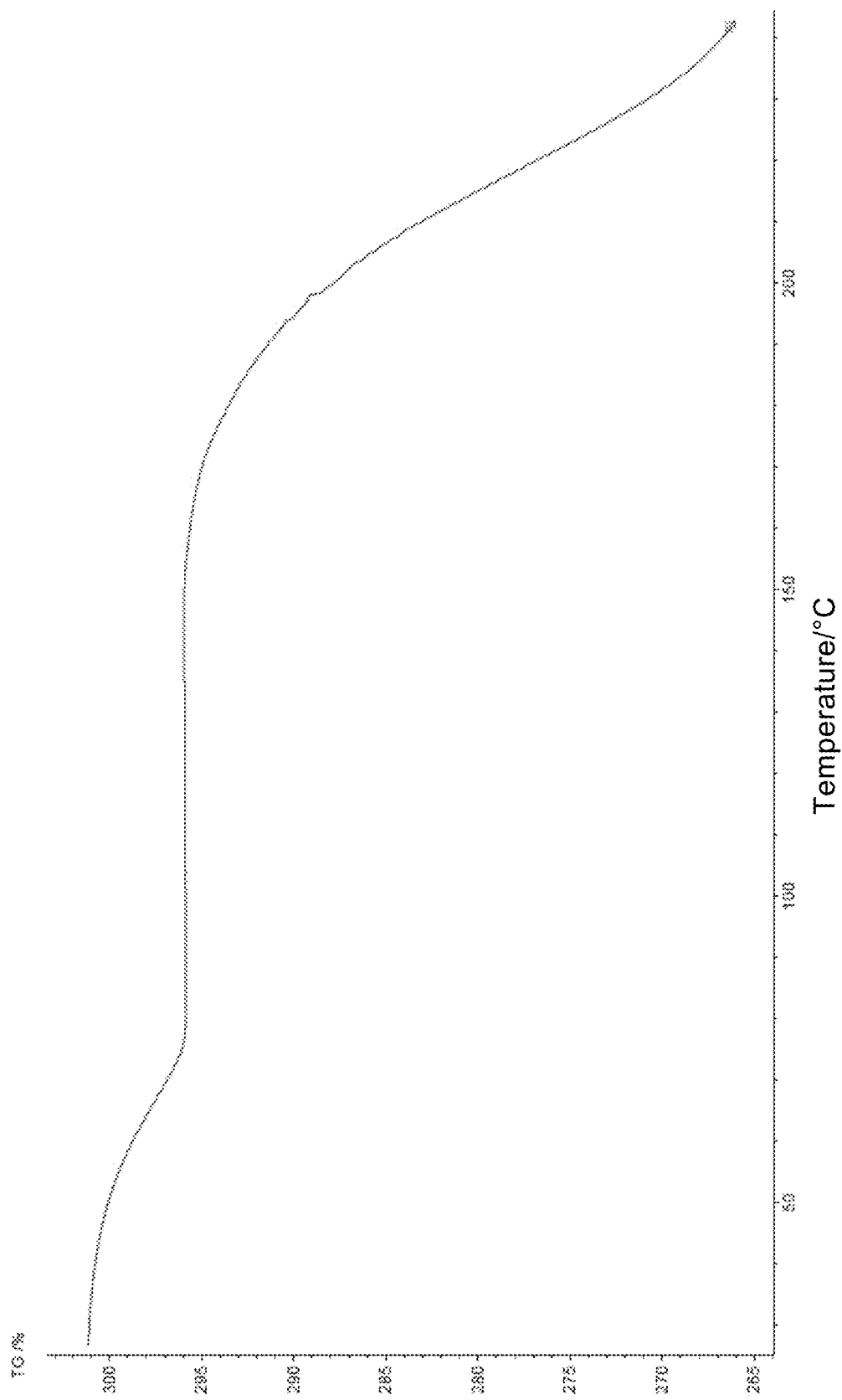
FIG. 15C: shows a TGA diagram of crystalline form of oclacitinib maleate (form B)
Figure 15D:
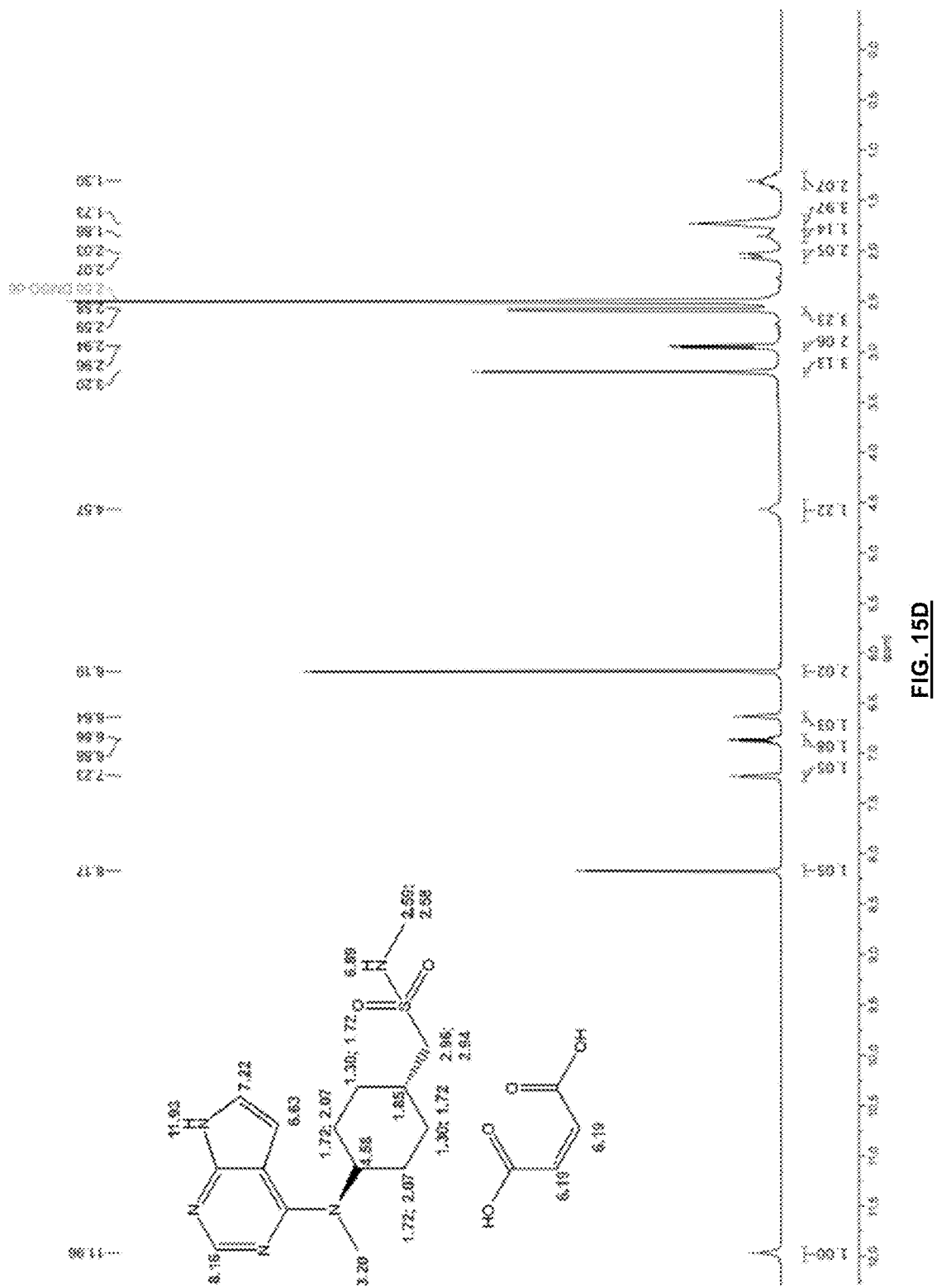
FIG. 15D: shows an 1H NMR spectrum of crystalline form of oclacitinib maleate (form B)

The crystalline form of oclacitinib maleate (form B) of the present invention can further be characterized by the TGA diagram as shown in FIG. 15C and/or the 1H-NMR spectrum shown in FIG. 15D.

Further, the present invention relates to a method for preparing crystalline form of oclacitinib maleate (form B) comprising the steps of:
X) dissolving oclacitinib base in ethanol and adding a mixture of maleic acid dissolved in mixture of water and ethanol;
Y) stirring the mixture of step X) to obtain a suspension; and
Z) filtering the suspension obtained in step Y).

In an embodiment of the method for preparing crystalline form of oclacitinib maleate (form B) of the present invention the method comprises the step of: after stirring the mixture in step Y), leaving the suspension for 10 hours to 20 hours, before performing step Z).

The present invention relates to amorphous oclacitinib maleate. It was found that the amorphous oclacitinib maleate was easy to separate within the production process. Amorphous oclacitinib maleate can be characterized by one of the x-ray powder diffraction patterns as shown in FIGS. 3-11.

The present invention also relates to a method for preparing amorphous oclacitinib maleate comprising the steps of:
a) dissolving oclacitinib maleate in a solvent to obtain a solution of oclacitinib maleate; and
b) evaporating the solution of oclacitinib maleate obtained in step a),
wherein the solvent comprises water and/or a water miscible solvent.

Step a) and/or step b) of the above method may be performed at a temperature of between 30° C. and 50° C., preferably between 35° C. and 45° C., more preferably about 40° C.

Further, step a) of the method for preparing amorphous oclacitinib maleate may further comprise the step of, after obtaining the solution of oclacitinib maleate, filtering the obtained solution of oclacitinib maleate.

The present invention also relates to a method for preparing amorphous oclacitinib maleate comprising the steps of:
i) dissolving oclacitinib maleate in a solvent to obtain a solution of oclacitinib maleate;
ii) cooling the solution of oclacitinib maleate obtained in step i) to a temperature of between 0° C. and 10° C., preferably between 2.5° C. and 7.5° C., more preferably about 5° C., to obtain a suspension; and
iii) filtering the suspension obtained in step ii),
wherein the solvent comprises water and/or a water miscible solvent.

Step i) of above method may further comprise the step of, after obtaining the solution of oclacitinib maleate, filtering the obtained solution of oclacitinib maleate.

Further, the above method may comprise the step of: after step i) and before step ii), leaving the solution of oclacitinib maleate obtained in step i) for at least 1 hour, preferably between 1 and 3 hours, more preferably about 2 hours.

The temperature used in the above method may be between 20° C. and 40° C., preferably between 25° C. and 35° C., more preferably about 30° C.

Step ii) of the above method may be performed at a cooling rate of 0.1° C./min.

The present invention also relates to a method for preparing amorphous oclacitinib maleate comprising the steps of:
x) dissolving oclacitinib maleate in a solvent to obtain a solution of oclacitinib maleate;
y) adding an anti-solvent to the solution of oclacitinib maleate obtained in step x) to obtain a suspension; and
z) filtering the suspension obtained in step y),
wherein the solvent comprises a water miscible solvent.

Step x) of the above method may be performed at a temperature of between 20° C. and 30° C., preferably at room temperature.

The present invention further relates to a method for preparing amorphous oclacitinib maleate comprising the steps of:
f) providing a mixture of oclacitinib maleate and a stabiliser;
g) dissolving oclacitinib maleate in a solvent to obtain a solution of oclacitinib maleate; and
h) evaporating the solution of oclacitinib maleate obtained in step g),
wherein the solvent comprises water and/or a water miscible solvent.

Step g) and/or step h) of the above method may be performed at a temperature of between 30° C. and 50° C., preferably between 35° C. and 45° C., more preferably about 40° C.

The evaporation step h) may be performed for 24-120 hours, preferably for 48-96 hours, more preferably about 72 hours.

Further, step g) of the method for preparing amorphous oclacitinib maleate may further comprise the step of, after obtaining the solution of oclacitinib maleate, filtering the obtained solution of oclacitinib maleate.

The present invention further relates to a stable amorphous oclacitinib maleate, wherein the stable amorphous oclacitinib maleate is stable under conditions having a relative humidity of at most 30%, preferably stable under conditions having a relative humidity of at most 25%. The stable amorphous oclacitinib maleate may be obtainable by the method comprising the steps of:

f) providing a mixture of oclacitinib maleate and a stabiliser;

g) dissolving oclacitinib maleate in a solvent to obtain a solution of oclacitinib maleate; and h) evaporating the solution of oclacitinib maleate obtained in step g), wherein the solvent comprises water and/or a water miscible solvent.

Step g) and/or step h) of the above method may be performed at a temperature of between 30° C. and 50° C., preferably between 35° C. and 45° C., more preferably about 40° C.

The evaporation step h) may be performed for 24-120 hours, preferably for 48-96 hours, more preferably about 72 hours.

Further, step g) of the method for preparing amorphous oclacitinib maleate may further comprise the step of, after obtaining the solution of oclacitinib maleate, filtering the obtained solution of oclacitinib maleate.

The anti-solvent may be selected form the group consisting of anisole, p-xylene, trimethylamine, 2-propanol, ethyl acetate, cyclohexane, 3-methyl-1-butanol, n-butyl acetate, diethyl ether, n-heptane, and combinations thereof.

The stabiliser may be selected from the group consisting of the free base of pharmaceutical active agents and pharmaceutical acceptable excipients. A preferred stabiliser is oclacitinib free base.

The term "water miscible solvent" as used herein, may include solvents selected from the group consisting of formamide, dimethyl sulfoxide, ethylene glycol, 1,3-propanediol, ethanol, acetone, pyridine, acetonitrile, methanol, tetramethyl urea, 1-pentanol, dichloromethane, tert-butanol, and combinations thereof.

The present invention further relates to a pharmaceutical composition comprising amorphous oclacitinib maleate. The pharmaceutical composition comprising amorphous oclacitinib maleate may be a pharmaceutical composition having an immediate release profile. It was found that by providing a pharmaceutical composition comprising amorphous oclacitinib maleate such pharmaceutical composition has a release profile which is much faster compared to the release profile of a pharmaceutical composition comprising oclacitinib maleate form A.

Figure 13A:
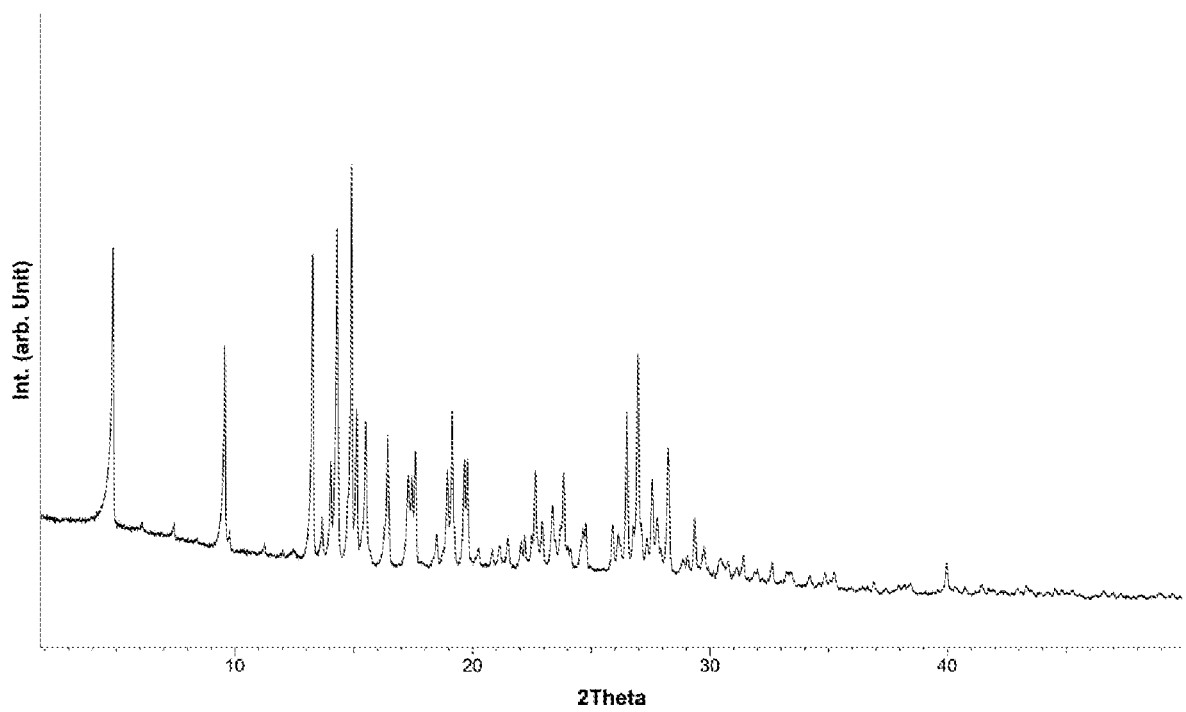
FIG. 13A: shows an x-ray powder diffraction pattern of crystalline tetramethyl urea solvate form of oclacitinib maleate.

The present invention relates to crystalline tetramethyl urea solvate form of oclacitinib maleate. It was found that the crystalline tetramethyl urea solvate form of oclacitinib maleate has improved properties in handling during the preparation of a pharmaceutical composition. Crystalline tetramethyl urea solvate form of oclacitinib maleate can be characterized by the x-ray powder diffraction pattern as shown in FIG. 13A.

The crystalline tetramethyl urea solvate form of oclacitinib maleate of the present invention may be characterized by having an x-ray powder diffraction pattern comprising a characteristic peak at about 4.87±0.2° 2θ. The crystalline tetramethyl urea solvate form of oclacitinib maleate can be further characterized by having an x-ray powder diffraction pattern comprising further characteristic peaks at about 16.44, 19.66, 19.79, and 27.57±0.2° 2θ.

Figure 13B:
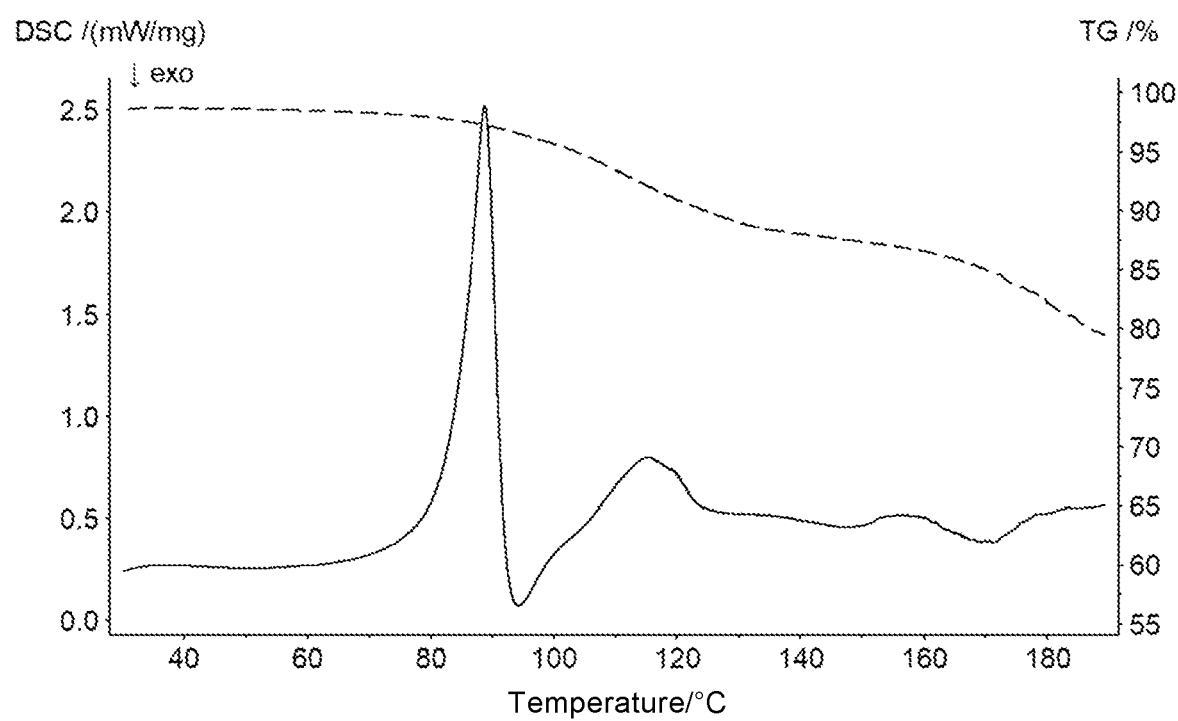
FIG. 13B: shows a Differential Scanning calorimetric (DSC) and Thermogravimetric Analysis (TGA) diagram of crystalline tetramethyl urea solvate form of oclacitinib maleate.

The crystalline tetramethyl urea solvate form of oclacitinib maleate of the present invention can further be characterized by the DSC and TGA diagram as shown in FIG. 13B.

The crystalline tetramethyl urea solvate form of oclacitinib maleate can be characterized by having a DSC exhibiting an endothermic peak at about 89° C. The crystalline tetramethyl urea solvate form of oclacitinib maleate can be further characterized by having a DSC further exhibiting an exothermic peak at about 94° C. and an endothermic peak at about 115° C.

Figure 13C:
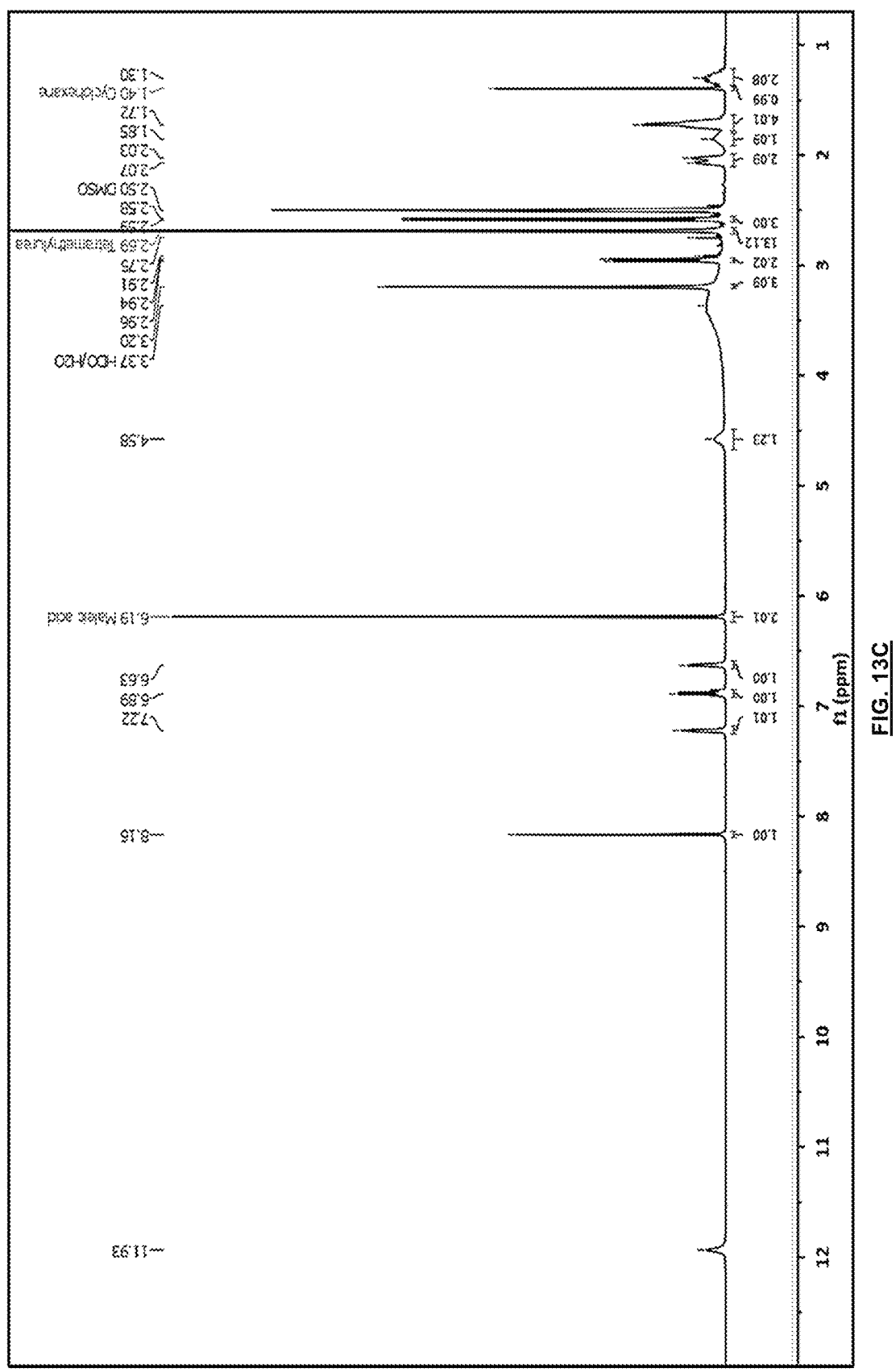
FIG. 13C: shows an 1H NMR spectrum of crystalline tetramethyl urea solvate form of oclacitinib maleate.

The crystalline tetramethyl urea solvate form of oclacitinib maleate of the present invention can further be characterized by the 1H-NMR spectrum shown in FIG. 13C.

The present invention also relates to a method for preparing crystalline tetramethyl urea solvate form of oclacitinib maleate comprising the steps of:

A) dissolving oclacitinib maleate in tetramethyl urea to obtain a solution of oclacitinib maleate;

B) adding an anti-solvent to the solution of oclacitinib maleate obtained in step A) to obtain a suspension; and C) filtering the suspension obtained in step B).

The anti-solvent as used in the method for preparing crystalline tetramethyl urea solvate form of oclacitinib maleate may be selected form the group consisting of anisole, p-xylene, trimethylamine, 2-propanol, ethyl acetate, cyclohexane, 3-methyl-1-butanol, n-butyl acetate, diethyl ether, n-heptane, and combinations thereof, preferably cyclohexane.

The method for preparing crystalline tetramethyl urea solvate form of oclacitinib maleate is preferably performed at a temperature of between 20° C. and 30° C., preferably at room temperature.

Figure 14A:
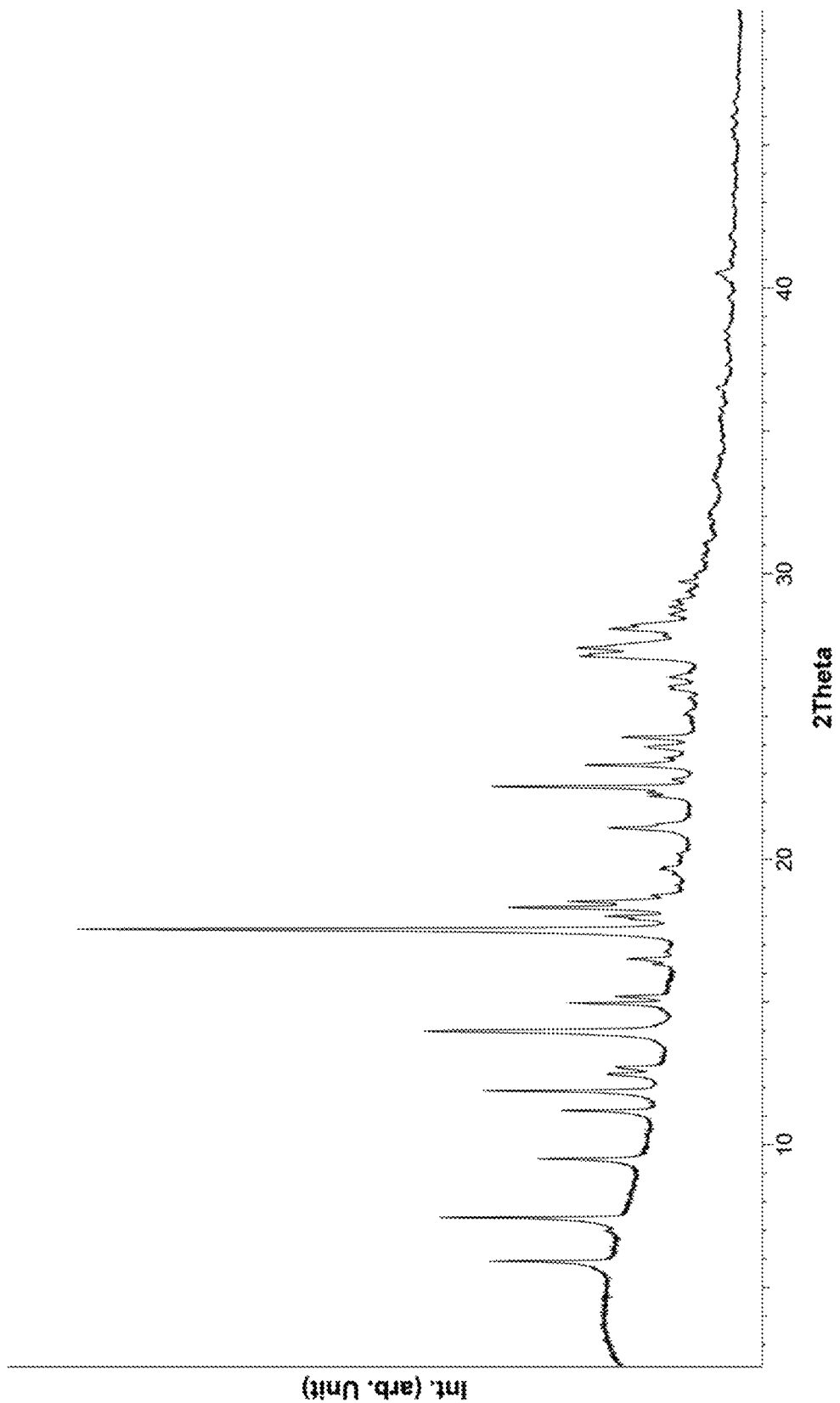
FIG. 14A: shows an x-ray powder diffraction pattern of crystalline monohydrate form of oclacitinib maleate.

The present invention relates to crystalline monohydrate form of oclacitinib maleate. It was found that the crystalline monohydrate form of oclacitinib maleate was easier to separate during the production process and/or has improved stability increasing the shelf-life of a pharmaceutical composition comprising the crystalline monohydrate form of oclacitinib maleate of the present invention. It was found that crystalline monohydrate form of oclacitinib maleate is stable and is not subjected to a conversion of solid state by storage of crystalline monohydrate form of oclacitinib maleate under relatively low relative humidity (<50% rH) as well as relatively high relative humidity (>50% rH). In fact it was found that crystalline monohydrate form of oclacitinib maleate is stable by any relative humidity of the surrounding air. Crystalline monohydrate form of oclacitinib maleate can be characterized by the x-ray powder diffraction pattern as shown in FIG. 14A.

The crystalline monohydrate form of oclacitinib maleate of the present invention may be characterized by having an x-ray powder diffraction pattern comprising a characteristic peak at about 5.93±0.2° 2θ. The monohydrate form of oclacitinib maleate can be further characterized by having an x-ray powder diffraction pattern comprising further characteristic peaks at about 11.90, 17.55, 22.55, and 27.40±0.2° 2θ.

Figure 14B:
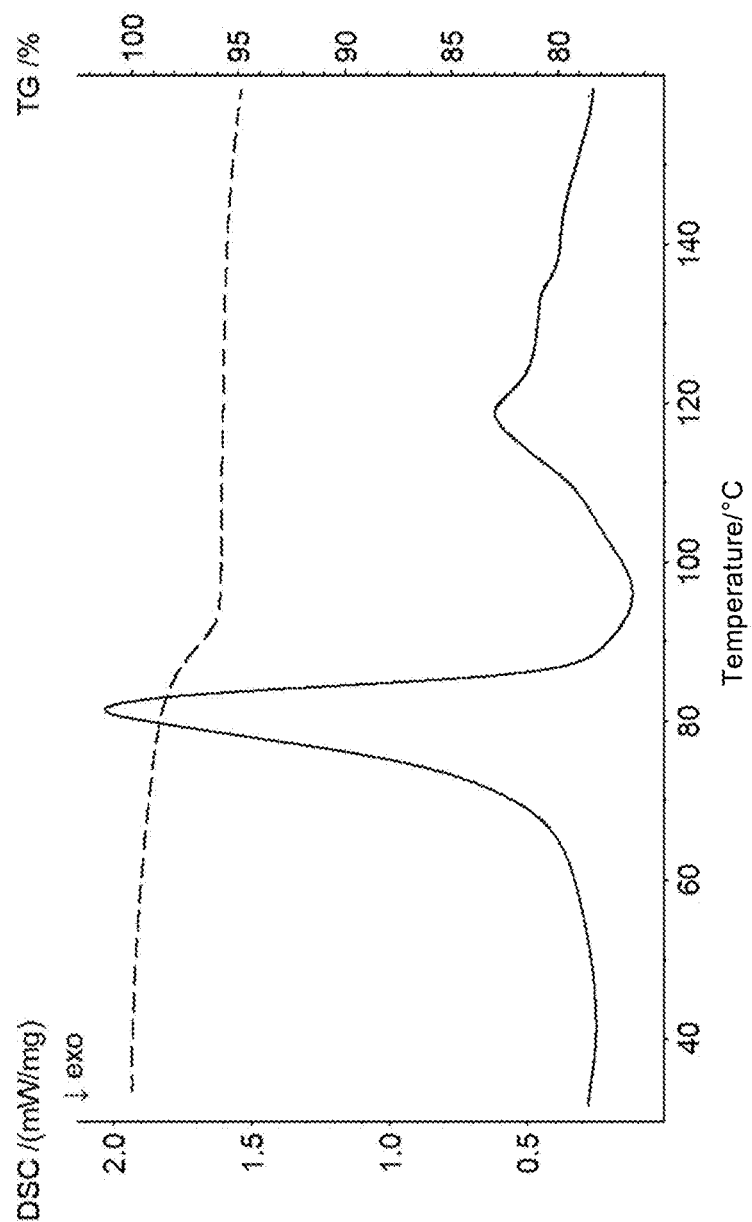
FIG. 14B: shows a DSC and TGA diagram of crystalline monohydrate form of oclacitinib maleate.

The crystalline monohydrate form of oclacitinib maleate of the present invention can further be characterized by the DSC and TGA diagram as shown in FIG. 14B.

The crystalline monohydrate form of oclacitinib maleate can be characterized by having a DSC exhibiting an endothermic peak at about 81° C. The crystalline monohydrate form of oclacitinib maleate can be further characterized by having a DSC further exhibiting an exothermic peak at about 96° C. and an endothermic peak at about 118° C.

Figure 14C:
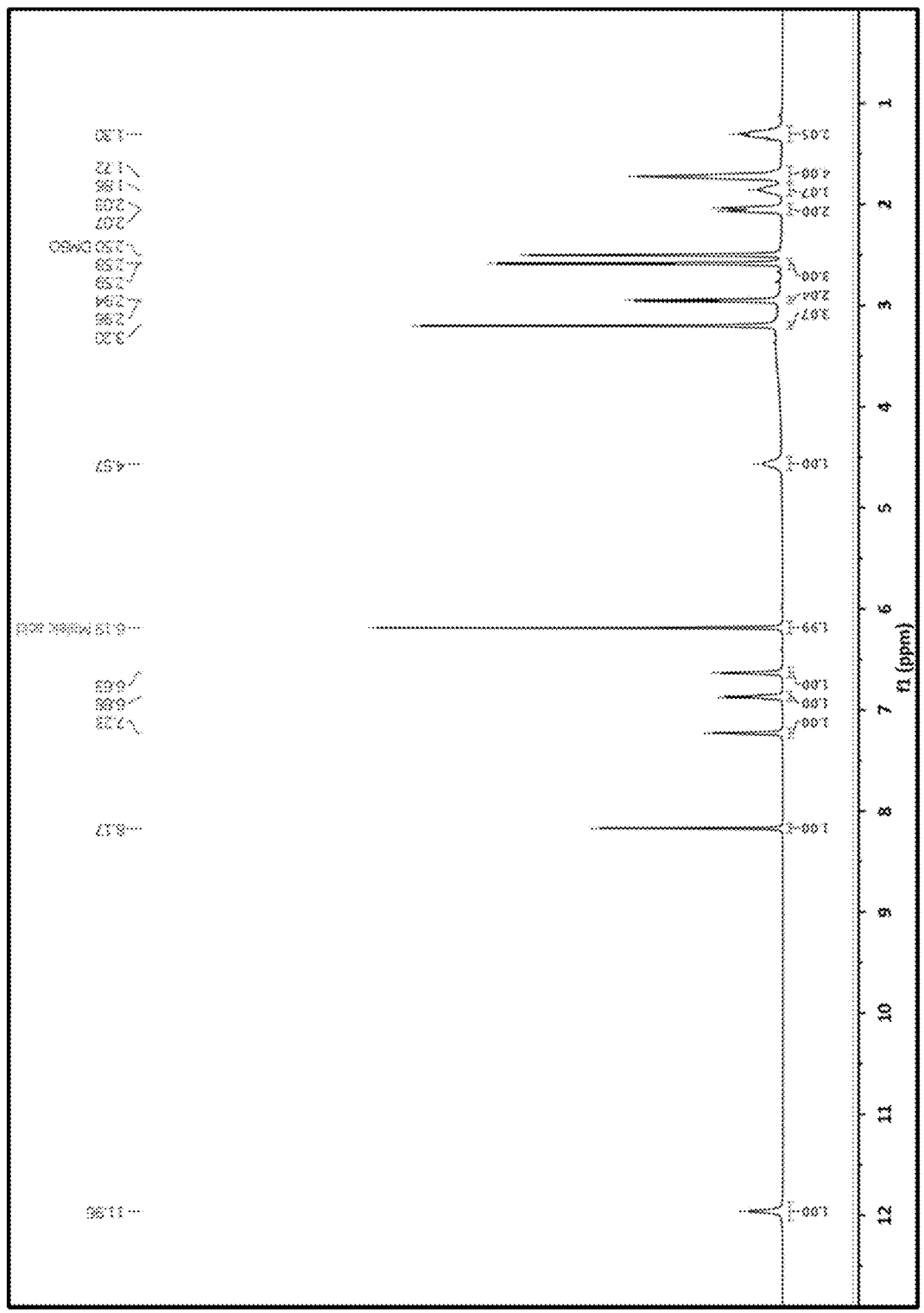
FIG. 14C: shows an 1H NMR spectrum of crystalline monohydrate form of oclacitinib maleate.

The crystalline monohydrate form of oclacitinib maleate of the present invention can further be characterized by the 1H-NMR spectrum shown in FIG. 14C.

The present invention further relates to a pharmaceutical composition comprising crystalline monohydrate form of oclacitinib maleate. The pharmaceutical composition comprising crystalline monohydrate form of oclacitinib maleate may be a pharmaceutical composition having a slow release profile. It was found that by providing a pharmaceutical composition comprising crystalline monohydrate form of oclacitinib maleate such pharmaceutical composition has a release profile which is slower compared to the release profile of a pharmaceutical composition comprising oclacitinib maleate form A.

The present invention also relates to a method for preparing crystalline monohydrate form of oclacitinib maleate comprising the step of grinding oclacitinib base with maleic acid at a grinding frequency of between 40 Hz and 60 Hz, preferably about 50 Hz.

The method for preparing crystalline monohydrate form of oclacitinib maleate by means of grinding may be performed at a temperature of between 20° C. and 30° C., preferably at room temperature for at least 10 minutes, preferably between 10 minutes and 30 minutes, more preferably about 15 minutes.

The method for preparing crystalline monohydrate form of oclacitinib maleate by means of grinding may further comprise the step of, after grinding oclacitinib base with maleic acid, leaving the obtained oclacitinib maleate for 48 hours to 72 hours to solidify.

The present invention also relates to a method for preparing crystalline monohydrate form of oclacitinib maleate comprising the steps of:

I) dissolving oclacitinib base and maleic acid to in a solvent to obtain a solution of oclacitinib maleate;

II) evaporating the solution of oclacitinib maleate obtained in step I) to obtain a suspension;

III) stirring the suspension obtained in step II) for at least 24 hours, preferably between 48 hours and 144 hours, more preferably for about 96 hours; and IV) filtering the stirred suspension obtained in step III), wherein the solvent comprises water and/or a water miscible solvent.

The method for preparing crystalline monohydrate form of oclacitinib maleate by means of evaporation may be performed at a temperature of between 20° C. and 30° C., preferably at room temperature.

The present invention relates to oclacitinib maleate containing at least 50% of the oclacitinib maleate according to the present invention, preferably at least 75% or at least 95%.

The term "the oclacitinib maleate according to the present invention" includes the oclacitinib maleate, i.e. crystalline form oclacitinib maleate (form b), crystalline monohydrate form of oclacitinib maleate, crystalline tetramethyl urea solvate form of oclacitinib maleate, amorphous oclacitinib maleate and combinations thereof.

The present invention relates to oclacitinib maleate, in particular oclacitinib maleate containing at least 50% of the oclacitinib maleate according to the present invention, for use in therapy.

The present invention relates to oclacitinib maleate, in particular oclacitinib maleate containing at least 50% of the oclacitinib maleate according to the present invention, for use in treating:

allergic reactions, allergic dermatitis, atopic dermatitis, eczema or pruritus in a mammal; and/or cancers, leukemia, lupus, multiple myeloma in a mammal.

The "mammal" as used herein may comprise companion animals, such as dogs, and/or livestock.

The present invention relates to a pharmaceutical composition comprising the oclacitinib maleate, in particular oclacitinib maleate containing at least 50% of the oclacitinib maleate according to the present invention, and a pharmaceutically acceptable carrier.

The present invention relates to a pharmaceutical composition comprising oclacitinib maleate, wherein the oclacitinib maleate contains at least 5% of the oclacitinib maleate according to the present invention, preferably at least 10%, at least 50% or at least 70%, more preferably at least 80% or at least 90%.

The present invention further relates to a set of pharmaceutical compositions, wherein the set of pharmaceutical compositions comprises one or more pharmaceutical compositions comprising crystalline monohydrate form of oclacitinib maleate and one or more pharmaceutical compositions comprising amorphous oclacitinib maleate. It was found that by providing a set of pharmaceutical compositions, a dosage regime can be designed wherein during the first 1 or 2 weeks the subject is treated with pharmaceutical compositions comprising amorphous oclacitinib maleate, followed by treating the subject with pharmaceutical compositions comprising crystalline monohydrate form of oclacitinib maleate. By combining the different release profiles of amorphous oclacitinib maleate (fast release) and crystalline monohydrate form of oclacitinib maleate (slow release) a more feasible and sustainable dosing regimen can be designed wherein the blood plasma concentration of oclacitinib is reached within a couple of days starting the initial administration of oclacitinib maleate. And wherein the blood plasma concentration of oclacitinib is maintained after the preferred blood plasma concentration is reached, using the slow release profile of crystalline monohydrate form of oclacitinib maleate.

EXAMPLES

X-Ray Powder Diffraction Measurement Method (Transmission Mode)

X-Ray Powder Diffraction (XRPD) data were obtained by placing each sample into a standard glass capillary (ø=0.7 mm), after careful grinding (with mortar and pestle). The measurement was performed at room temperature with a Bruker D8 Advance Diffractometer (Cu-$K_\alpha$1=1.54059 Å, Johansson primary beam monochromator, position sensitive detector) in transmission mode with rotation of the sample. Data were collected in a 2θ range of 3-50°. The tube voltage and current were set to 40 kV and 40 mA, respectively.

X-Ray Powder Diffraction Measurement Method (Reflection Mode)

XRPD data were obtained by placing each sample onto a special zero-background silicon wafer, after careful grinding (with mortar and pestle). The measurement was performed at room temperature with a Bruker D2 Phaser Diffractometer (Cu-$K_\alpha$1/2=1.5418 Å, position sensitive detector) in reflection (Bragg-Brentano) mode with axial rotation of the sample. The data was collected in a 2θ range of 5-50°. The tube voltage and current were set to 30 kV and 10 mA, respectively.

Differential Scanning Calorimetry

Differential Scanning calorimetric (DSC) analysis was performed with a Netzsch Phoenix DSC 204 F1. Approximately 5-15 mg of each sample was placed into a DSC pan and weight accurately recorded. Sealed aluminum pans with one pinhole were used for analysis. The samples were heated under nitrogen atmosphere at a rate of 10° C./min.

Thermal Gravimetric Analysis

Thermogravimetric Analysis (TGA) was performed using a Perkin Elmer Thermogravimetric Analyzer Pyris 6 TGA. Approximately 10-15 mg of sample was placed in a tared pan and weighted accurately in the TG furnace. The samples were heated in nitrogen at a rate of 10° C./min, up to a final temperature of 350° C.

Nuclear Magnetic Resonance

1H NMR spectra were acquired on a Bruker Advance DRX 400 spectrometer (at 400 MHz) at room temperature in deuterated solvent ($d_6$-DMSO). Information about the chemical shift δ is given in ppm, relative to the irradiation frequency. The signal of the deuterated solvent is used as internal standard.

Stability Tests

The stability of the solid forms of oclacitinib obtained was tested at three different conditions, i.e. storage at 25° C. at 0% relative humidity, 40° C. at 75% rH and 25° C. at 100% rH. Alternatively or additionally, the stability of the solid forms of oclacitinib obtained was tested at 25° C. at 25% rH.

Starting Materials

Oclacitinib Maleate Form A

Figure 1:
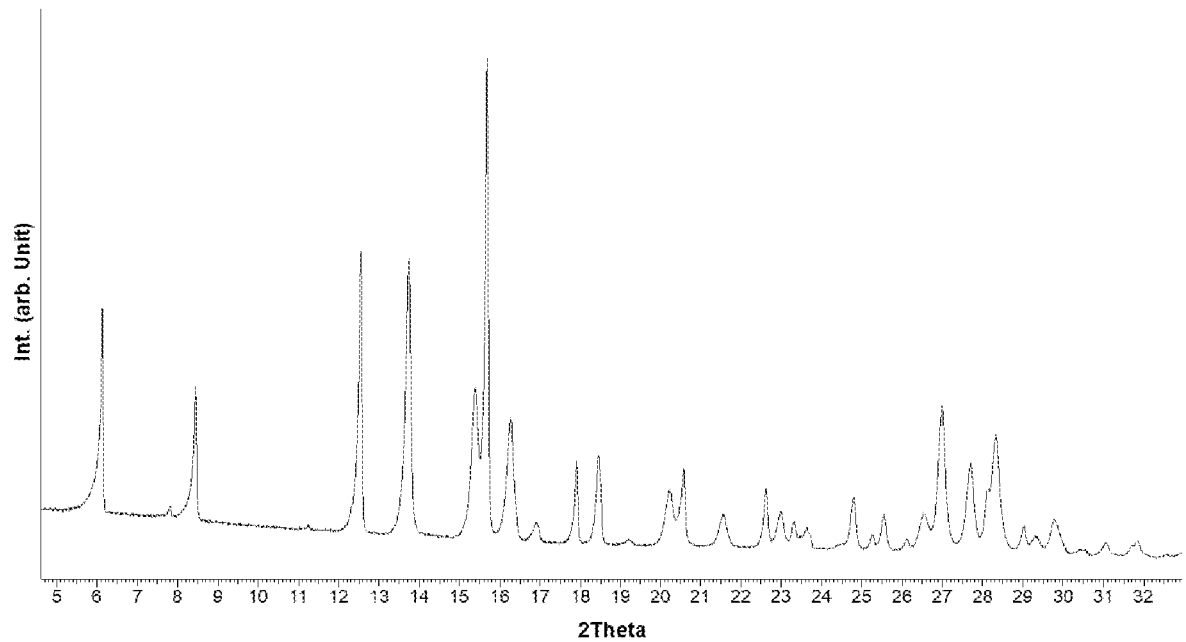
FIG. 1: shows an x-ray powder diffraction pattern of crystalline oclacitinib maleate form A.

Oclacitinib maleate form A was obtained by performing Example 1 b of European patent application no. 09786882.2 by providing a mixture of N-methyl-1-{trans-4-[methyl(7H-pyrrolo[2,3-d]pyrimidin-4-yl)amino]cyclohexyl}methanesulfonamide (212.0 g, 628.3 mmol) and maleic acid (67.2 g, 579.0 mmol) in 1-butanol (3200 ml) and water (400 ml) stirred at room temperature for 18 h. The mixture was reduced in volume to 1600 ml, via vacuum distillation (55° C., 100 mbar) and then cooled to 0° C. The resulting solid was collected by filtration, washed with heptane (500 ml) and dried in vacuo at 35° C. to give the maleate salt of N-methyl-1-{trans-4-[methyl(7H-pyrrolo[2,3-d]pyrimidin-4-yl)amino]-cyclohexyl}methanesulfonamide (253.0 g) as a crystalline form. The resulting solid was analyzed by XRPD (FIG. 1) conforming the formation of oclacitinib maleate form A (see also: FIG. 1, European patent application no. 09786882.2).

Oclacitinib Maleate Base

Figure 2:
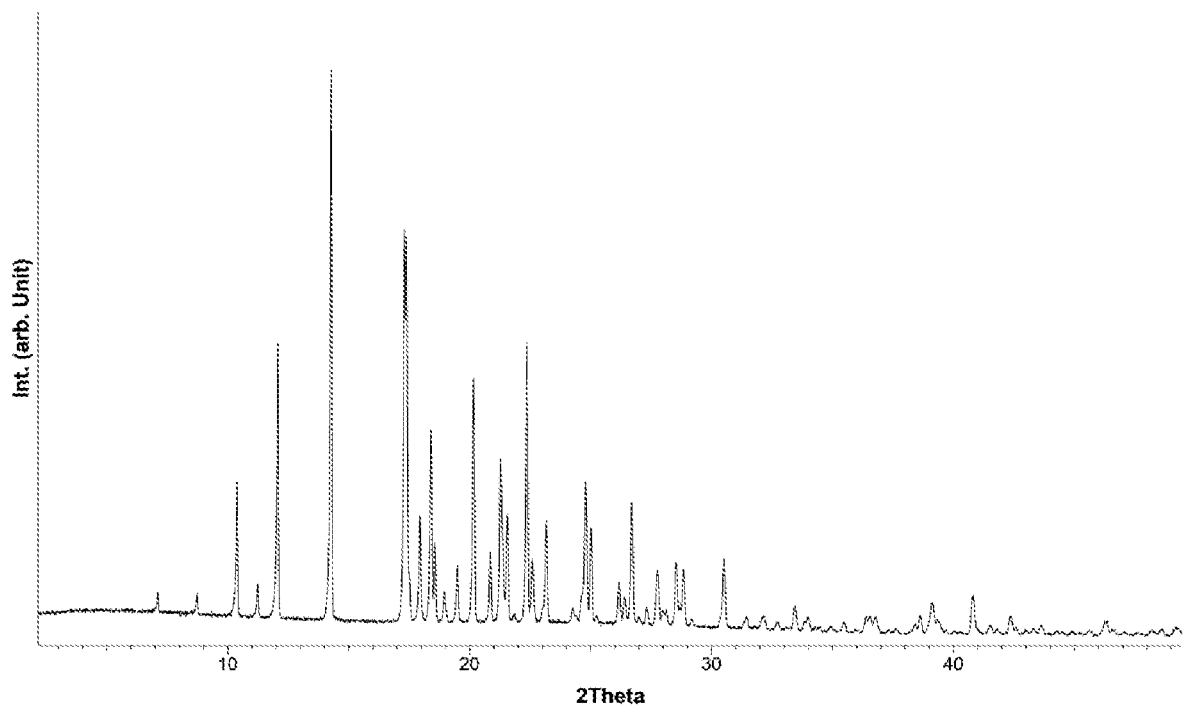
FIG. 2: shows an x-ray powder diffraction pattern of crystalline oclacitinib base.

Oclacitinib maleate base was purchased from Ningbo Noubai Pharmaceutical Co. Ltd. the solid was analysed by XRPD (FIG. 2).

Amorphous Oclacitinib Maleate

EXAMPLE 1

Figure 3:
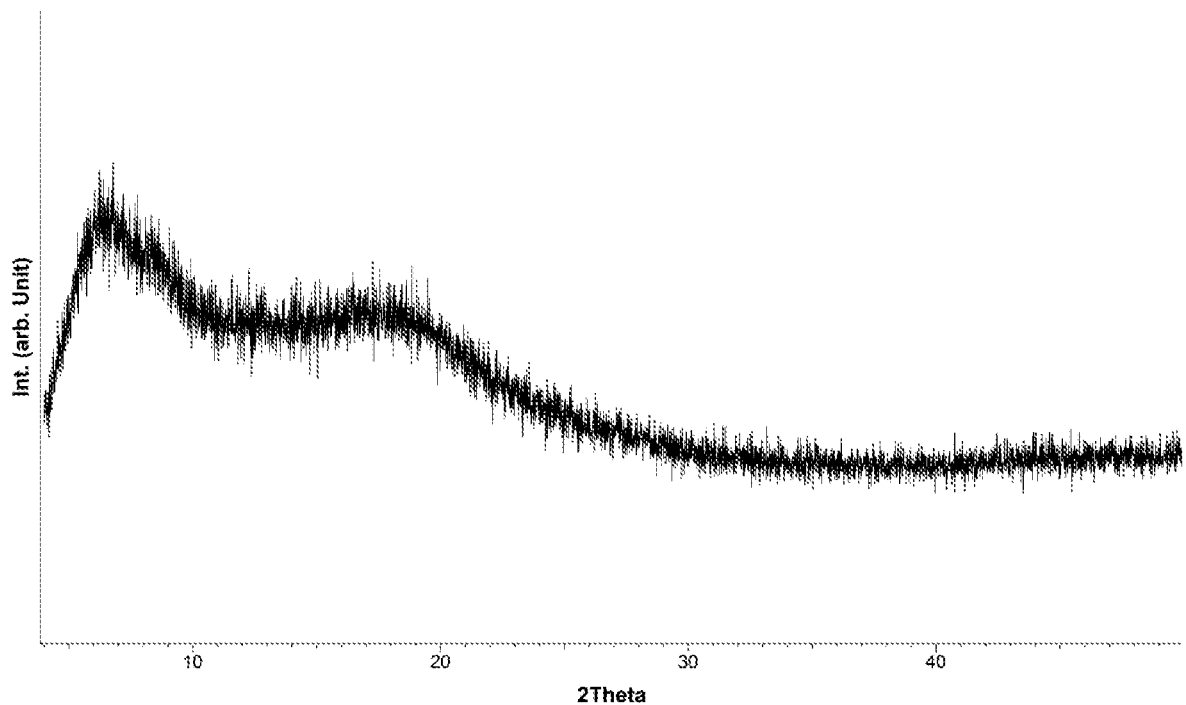
FIG. 3: shows an x-ray powder diffraction pattern of amorphous oclacitinib maleate.

Amorphous oclacitinib maleate was obtained by dissolving 36 mg of oclacitinib maleate (Form A) in 7 mL of water at 40° C. The solution was filtered through a ReZist syringe filter (PTFE, 0.2 µm) and was left for evaporation at 40° C. The resulting solid was analyzed by XRPD (FIG. 3).

EXAMPLE 2

Figure 4:
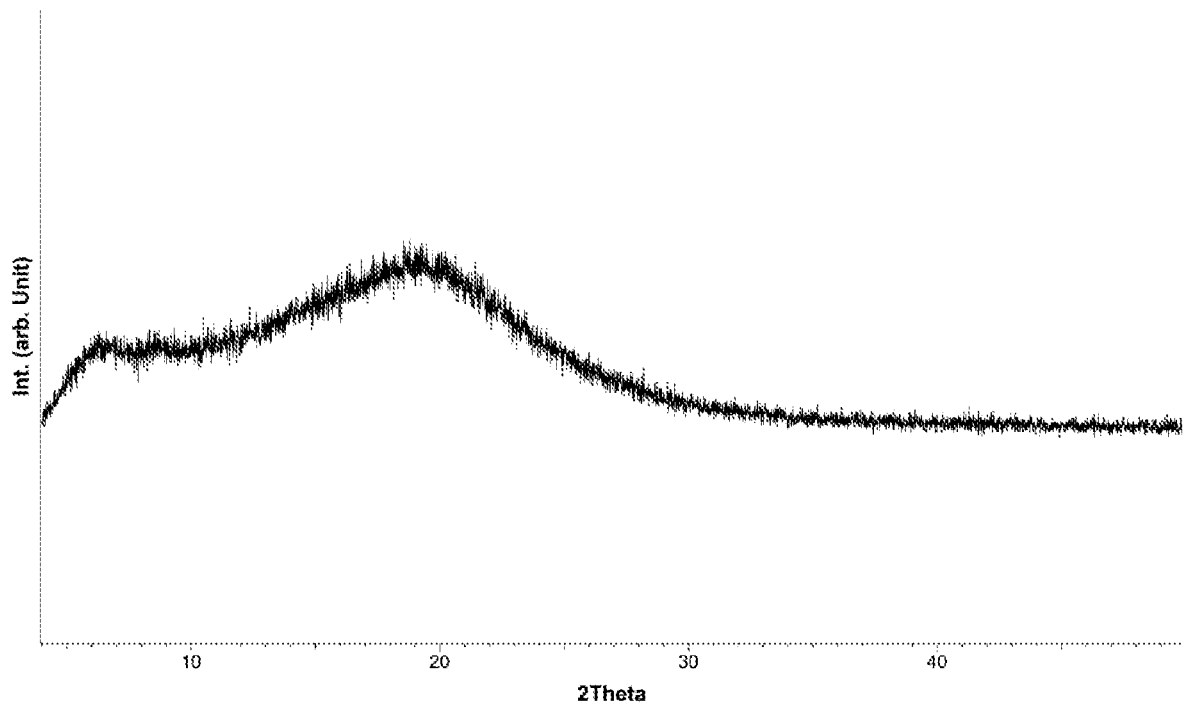
FIG. 4: shows an x-ray powder diffraction pattern of amorphous oclacitinib maleate.

Amorphous oclacitinib maleate was obtained by dissolving 40 mg of oclacitinib maleate (Form A) in 150 µL of DMSO at 40° C. The solution was filtered through a ReZist syringe filter (PTFE, 0.2 µm) and was left for evaporation at 40° C. The resulting solid was analyzed by XRPD (FIG. 4).

EXAMPLE 3

Figure 5:
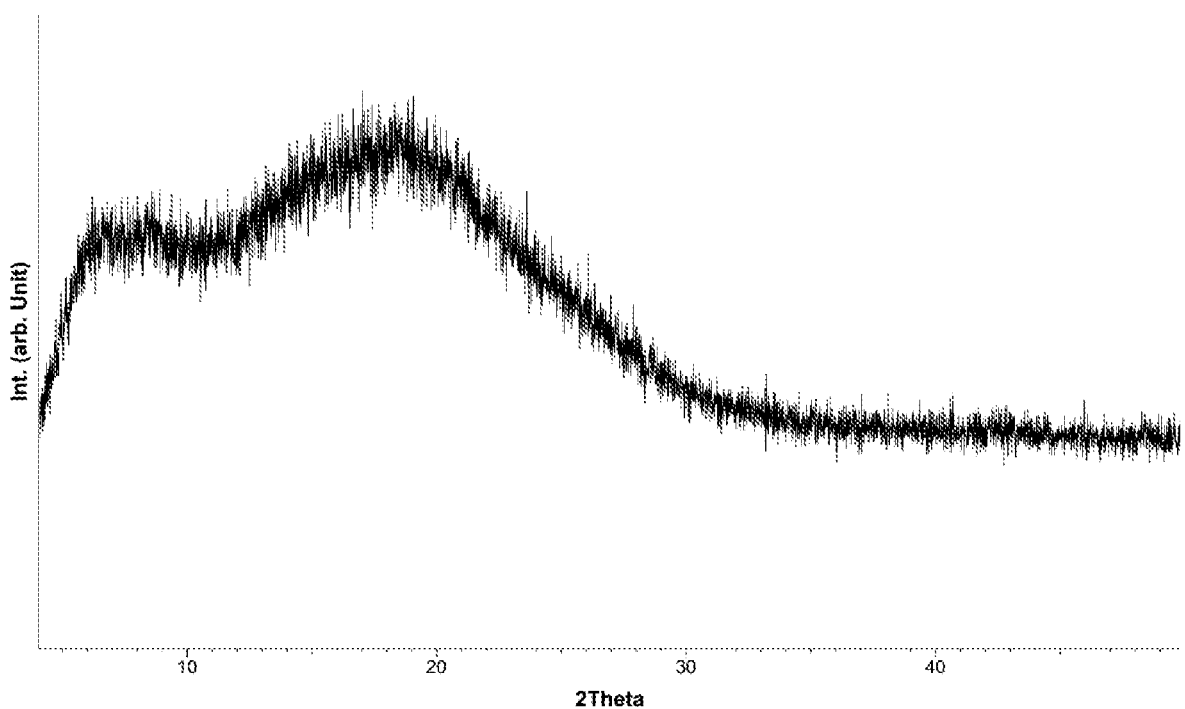
FIG. 5: shows an x-ray powder diffraction pattern of amorphous oclacitinib maleate.

Amorphous oclacitinib maleate was obtained by dissolving 39 mg of oclacitinib maleate (Form A) in 6 mL of acetonitrile at 40° C. The solution was filtered through a ReZist syringe filter (PTFE, 0.2 µm) and was left for evaporation at 40° C. The resulting solid was analyzed by XRPD (FIG. 5).

EXAMPLE 4

Figure 6:
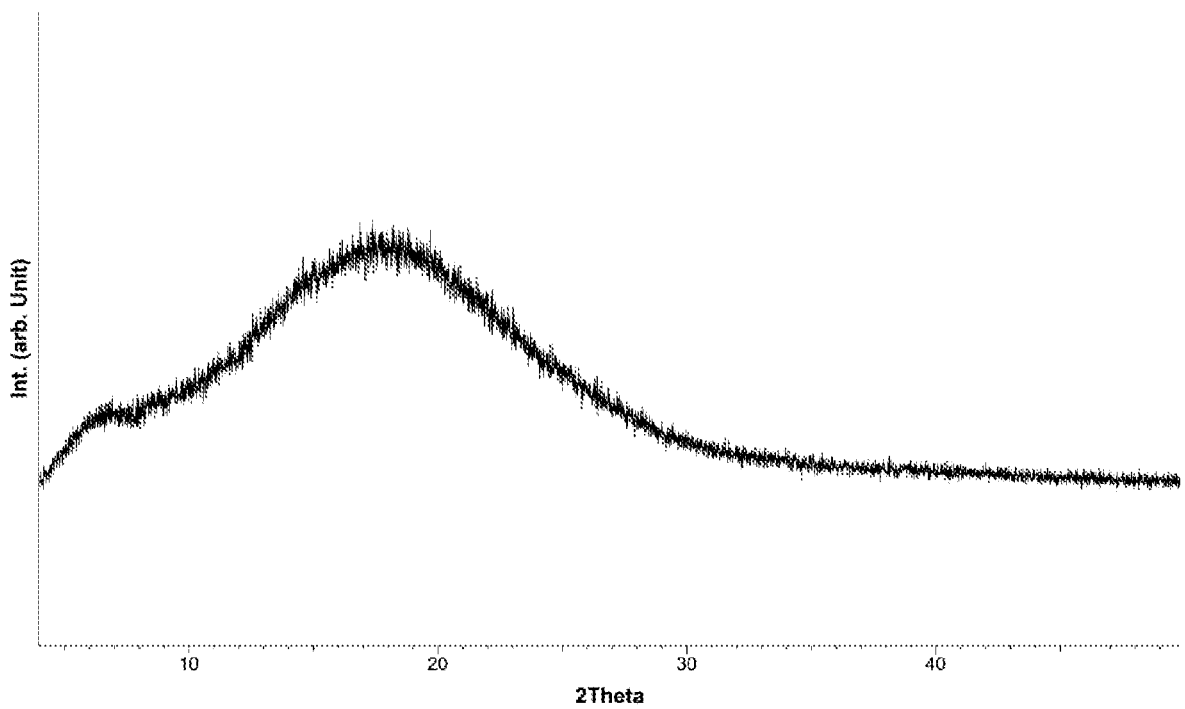
FIG. 6: shows an x-ray powder diffraction pattern of amorphous oclacitinib maleate.

Amorphous oclacitinib maleate was obtained by dissolving 40 mg of oclacitinib maleate (Form A) in 500 µL of tetramethyl urea at 40° C. The solution was filtered through a ReZist syringe filter (PTFE, 0.2 µm) and was left for evaporation at 40° C. The resulting solid was analyzed by XRPD (FIG. 6).

EXAMPLE 5

Figure 7:
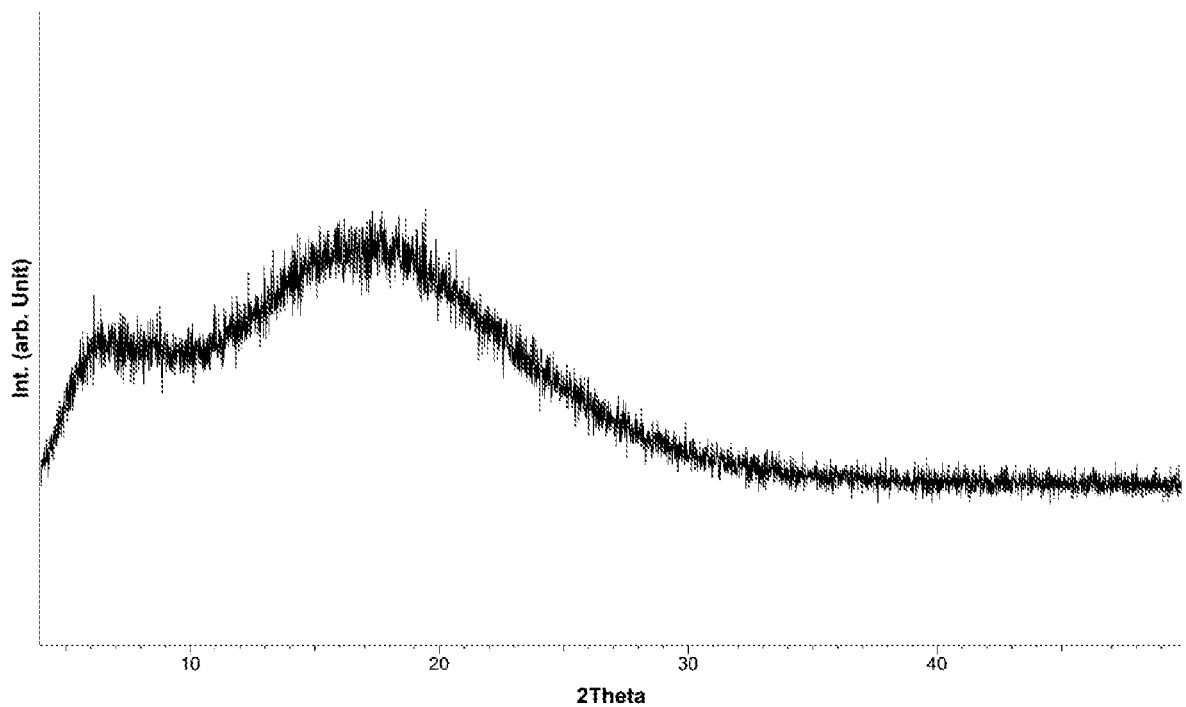
FIG. 7: shows an x-ray powder diffraction pattern of amorphous oclacitinib maleate.

Amorphous oclacitinib maleate was obtained by dissolving 41 mg of oclacitinib maleate (Form A) in 0.5 mL of tetramethyl urea at 30° C. The solution was filtered through a ReZist syringe filter (PTFE, 0.2 µm), and, after leaving the solution at 30° C. for 2 h, it was cooled to 5° C. at a cooling rate of 0.1° C./min. The resulting solid was isolated by filtration and analyzed by XRPD (FIG. 7).

EXAMPLE 6

Figure 8:
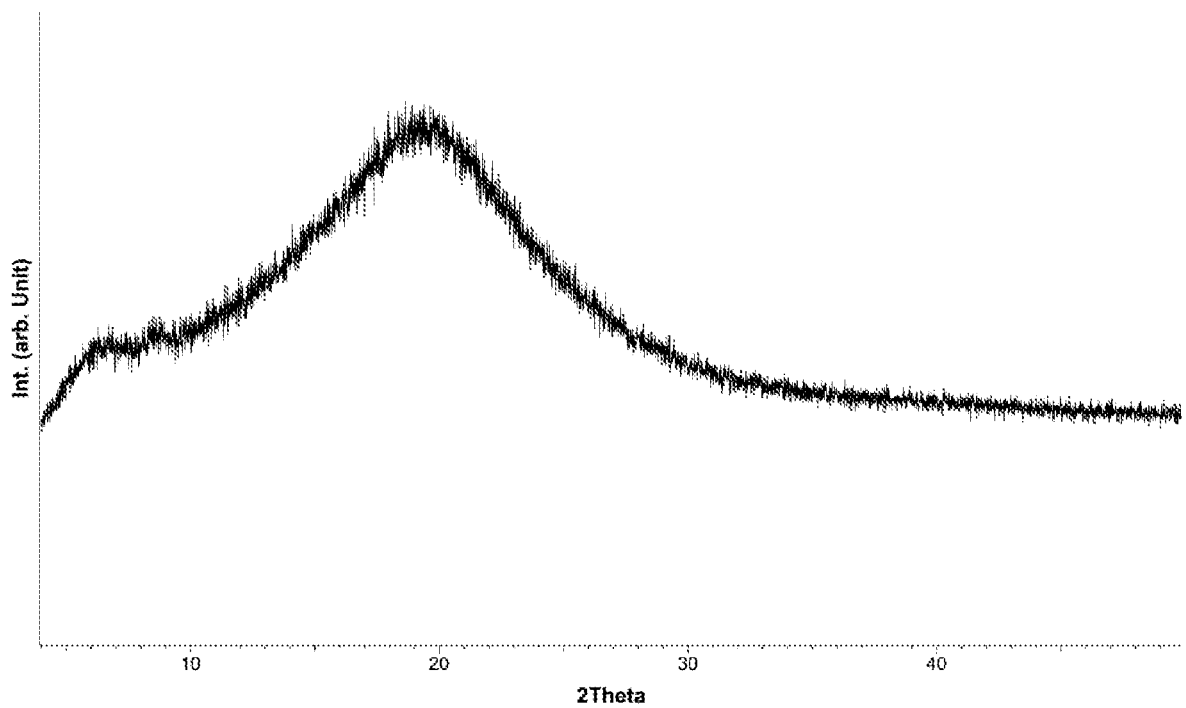
FIG. 8: shows an x-ray powder diffraction pattern of amorphous oclacitinib maleate.

Amorphous oclacitinib maleate was obtained by dissolving 39 mg of oclacitinib maleate (Form A) in 200 µL of DMSO at RT. 5 mL of n-heptane were then added to the solution, causing amorphous oclacitinib maleate to precipitate. The resulting solid was isolated by filtration and analyzed by XRPD (FIG. 8).

EXAMPLE 7

Figure 9:
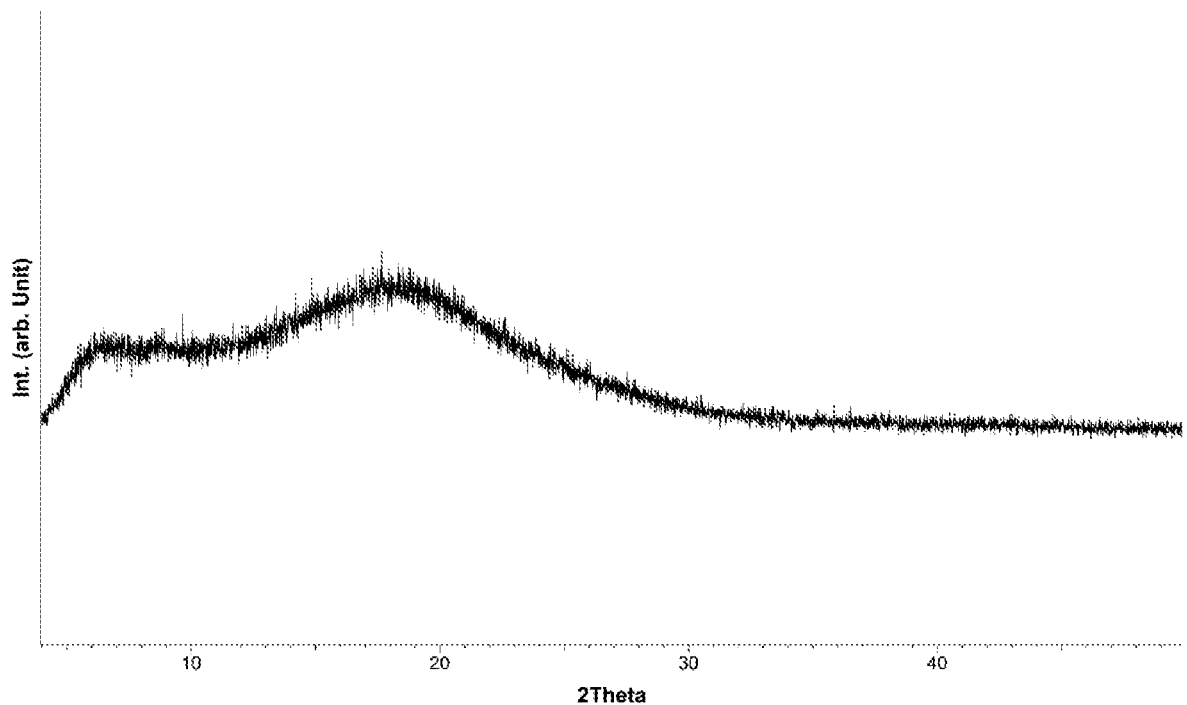
FIG. 9: shows an x-ray powder diffraction pattern of amorphous oclacitinib maleate.
Figure 10:
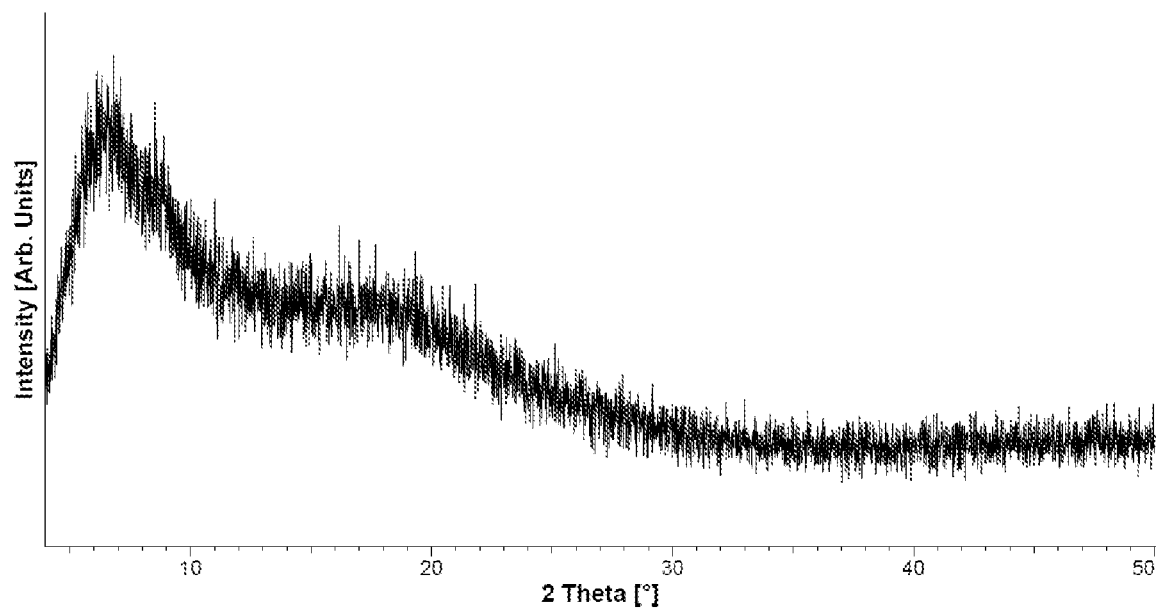
FIG. 10: shows an x-ray powder diffraction pattern of amorphous oclacitinib maleate.

Amorphous oclacitinib maleate was obtained by dissolving 41 mg of oclacitinib maleate (Form A) in 2 mL of methanol at RT. 7 mL of cyclohexane were then added to the solution, causing amorphous oclacitinib maleate to precipitate. The resulting solid was isolated by filtration and analyzed by XRPD (FIG. 9).

EXAMPLE 8

In order to provide an alternative method of preparing amorphous oclacitinib maleate, as a starting material mixtures of oclacitinib base and oclacitinib maleate were prepared. An overview of the mixtures prepared is provided in table 1.

TABLE 1

| | Starting material mixtures | |
|---|---|---|
| Example | Oclacitinib base (mg/mass ratio in %) | Oclacitinib maleate (mg/mass ratio in %) |
| 8a | 1.0/5 | 19.0/95 |
| 8b | 0.5/2.5 | 19.5/97.5 |
| 8c | 1.6/4.3 | 35.2/95.7 |

Amorphous oclacitinib maleate was obtained by dissolving the mixture of oclacitinib base and oclacitinib maleate in 3 mL acetonitrile at 40° C. After complete dissolution, the mixture was filtered through a ReZist syringe filter (PTFE, 0.2 µm) and the solvent was completely evaporated at 40° C. over 3 days. The resulting solid was analyzed by XRPD. As a representative example, FIG. 10 discloses the XRPD of the solids obtained by example 8.

EXAMPLE 9 (Comparative Example)

Figure 11:
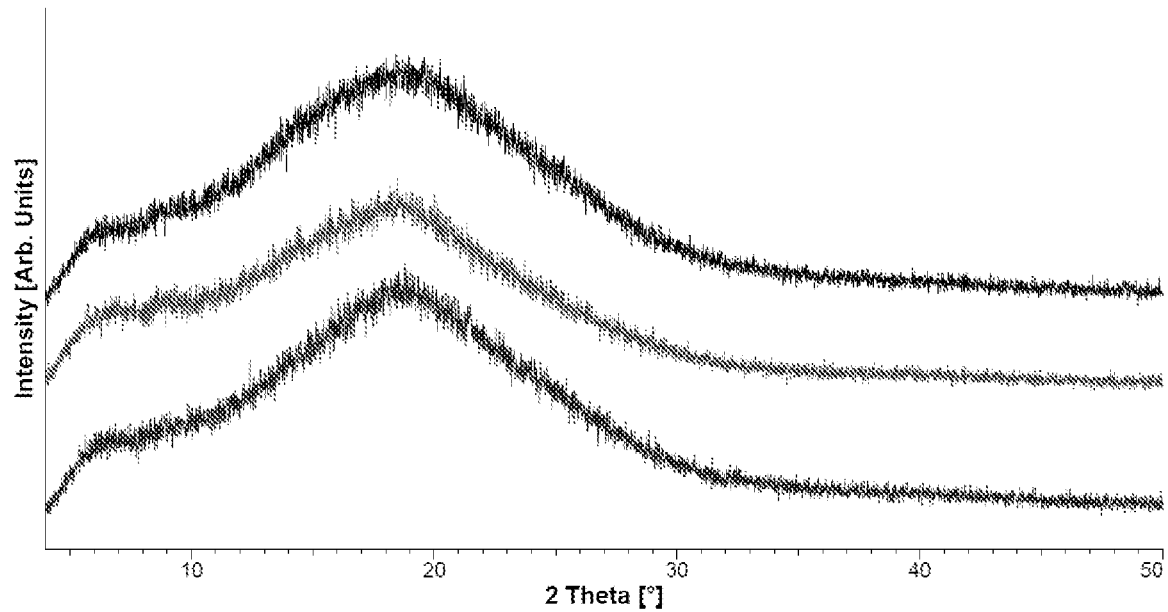
FIG. 11: shows an x-ray powder diffraction pattern of amorphous oclacitinib maleate.

Amorphous oclacitinib maleate was obtained by dissolving 22 mg oclacitinib maleate in 3 mL acetonitrile at 40° C. After complete dissolution, the mixture was filtered through a ReZist syringe filter (PTFE, 0.2 μm) and the solvent was completely evaporated at 40° C. over 3 days. The experiment was repeated 2 times and the resulting solid was analyzed by XRPD (FIG. 11).

Stability Tests

Figure 12A:
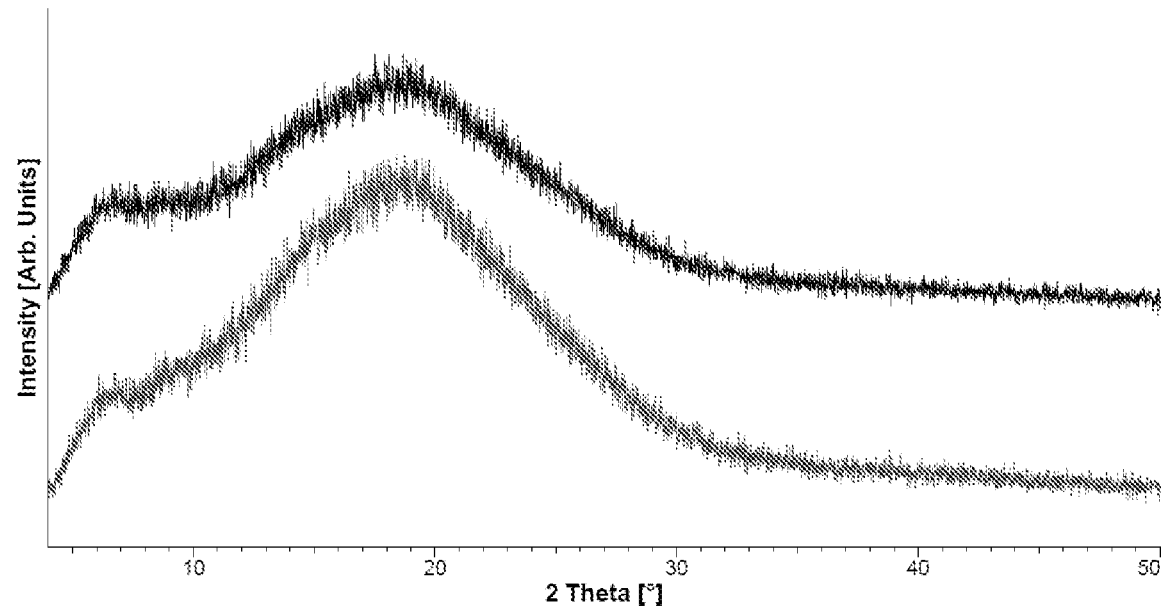
FIG. 12A: shows an x-ray powder diffraction pattern of amorphous oclacitinib maleate stored for 3 weeks at 25° C. at 25% rH.
Figure 12B:
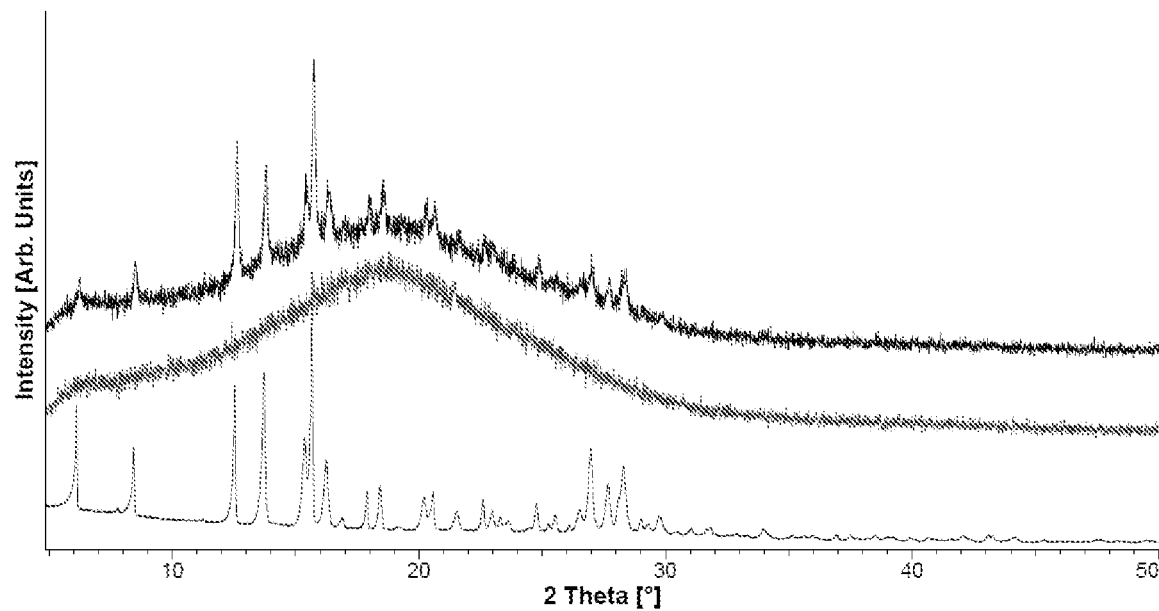
FIG. 12B: shows an x-ray powder diffraction pattern of amorphous oclacitinib maleate stored for 3 weeks at 25° C. at 25% rH.

The stability of amorphous oclacitinib maleate obtained by examples 8 and 9 was compared after storing the amorphous oclacitinib maleate at 25° C. at 25% rH by analysing the stored samples by XRPD. The XRPD of the amorphous oclacitinib maleate obtained by example 8 (FIG. 12A) does not show any change of solid state between the starting point (lower graph) and the solid after 3 weeks of storage (upper graph). The XRPD of the amorphous oclacitinib maleate obtained by example 9 (FIG. 12B) does show a transformation of the starting point (intermediate graph) to a mixture (upper graph) comprising amorphous oclacitinib maleate and oclacitinib maleate form A (see also: lower reference graph).

Figure 12C:
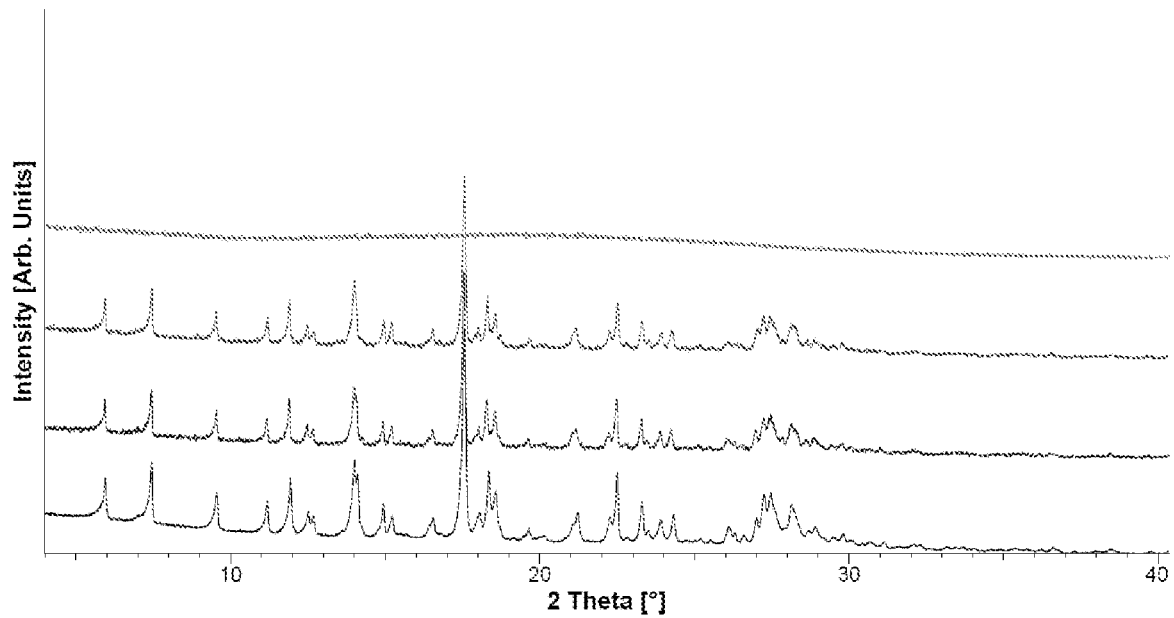
FIG. 12C: shows an x-ray powder diffraction pattern of amorphous oclacitinib maleate stored for 1 week under different storage conditions.

The stability of the amorphous oclacitinib maleate obtained by example 8 was further tested at the three different conditions as defined above. The XRPD (FIG. 12C) analysis of the samples after 2 weeks show a conversion (intermediate graphs) of the amorphous phase to the monohydrate form of oclacitinib maleate (see also: lower reference graph) at conditions having a relatively high humidity (i.e. 40° C. at 75% rH and 25° C. at 100% rH). Whereas the amorphous oclacitinib maleate obtained by example 8 remains stable (upper graph) at a relatively low humidity (i.e. 25° C. at 0% rH).

Tetramethyl Urea Solvate Form of Oclacitinib Maleate

EXAMPLE 10

Tetramethyl urea solvate form of oclacitinib maleate was obtained by dissolving 40 mg of oclacitinib maleate (Form A) in 0.8 mL of tetramethyl urea at RT. 3 mL of cyclohexane were then added to the solution, causing the solvate to precipitate. The resulting solid was isolated by filtration and analysed by XRPD (FIG. 13A), DSC (FIG. 13B), TGA (FIG. 13B) and NMR (FIG. 13C). Peak listing of the XRPD results of FIG. 13A are provided in table 2 (peak listing between 3 and 30° 2θ).

TABLE 2

| Name | 2θ | Relative Intensity |
|---|---|---|
| Peak #1 | 4.87° | 73.4% |
| Peak #2 | 6.08° | 4.3% |
| Peak #3 | 7.43° | 4.9% |
| Peak #4 | 9.57° | 51.5% |
| Peak #5 | 9.78° | 5.4% |
| Peak #6 | 11.24° | 2.9% |
| Peak #7 | 12.04° | 1.2% |
| Peak #8 | 12.44° | 1.9% |
| Peak #9 | 13.28° | 76.9% |
| Peak #10 | 13.67° | 10.5% |
| Peak #11 | 14.04° | 24.9% |
| Peak #12 | 14.31° | 84.0% |
| Peak #13 | 14.91° | 100.0% |
| Peak #14 | 15.13° | 38.7% |
| Peak #15 | 15.51° | 35.9% |
| Peak #16 | 16.44° | 32.8% |
| Peak #17 | 17.31° | 23.1% |
| Peak #18 | 17.46° | 23.0% |
| Peak #19 | 17.60° | 29.1% |
| Peak #20 | 18.51° | 8.0% |
| Peak #21 | 18.95° | 24.3% |
| Peak #22 | 19.15° | 39.4% |
| Peak #23 | 19.66° | 26.9% |
| Peak #24 | 19.79° | 26.8% |
| Peak #25 | 20.26° | 4.6% |
| Peak #26 | 20.84° | 4.5% |
| Peak #27 | 21.15° | 5.3% |
| Peak #28 | 21.51° | 7.6% |
| Peak #29 | 22.05° | 6.7% |
| Peak #30 | 22.19° | 8.0% |
| Peak #31 | 22.51° | 7.8% |
| Peak #32 | 22.65° | 24.5% |
| Peak #33 | 22.94° | 11.7% |
| Peak #34 | 23.38° | 16.1% |
| Peak #35 | 23.73° | 10.8% |
| Peak #36 | 23.85° | 24.1% |
| Peak #37 | 24.16° | 4.4% |
| Peak #38 | 24.66° | 10.4% |
| Peak #39 | 24.77° | 12.1% |
| Peak #40 | 25.92° | 11.7% |
| Peak #41 | 26.16° | 9.2% |
| Peak #42 | 26.50° | 39.8% |
| Peak #43 | 26.77° | 11.3% |
| Peak #44 | 26.97° | 54.9% |
| Peak #45 | 27.36° | 8.2% |
| Peak #46 | 27.57° | 23.2% |
| Peak #47 | 27.79° | 13.6% |
| Peak #48 | 28.25° | 31.2% |
| Peak #49 | 28.87° | 3.6% |
| Peak #50 | 29.06° | 4.5% |
| Peak #51 | 29.36° | 14.0% |
| Peak #52 | 29.75° | 7.2% |

The DSC analysis has been performed at a heating rate of 10 K/min. The thermogram (FIG. 13B) shows an endothermal peak at 89° C., followed by an exothermal event at 94° C. Subsequently a broad endothermal event occurs with two peaks at 115° C. and 119° C. Decomposition can be observed after about 150° C.

The TG analysis of oclacitinib maleate revealed a mass loss of 10% between 75 and 140° C. (FIG. 13B).

The 1H NMR analysis (FIG. 13C) did not show any indication for the presence of additional impurities other than some residual cyclohexane. The ratio of oclacitinib: maleic acid:tetramethyl urea was determined to be 1:1:1.

Stability tests

The stability of tetramethyl urea solvate form of oclacitinib maleate obtained by example 10 was tested at the three different conditions as defined above. The results of stability test are shown in table 3. In table 3, "tetramethyl urea solvate form of oclacitinib maleate" is abbreviated by "TMU solvate".

TABLE 3

Stability test results of tetramethyl urea solvate form of oclacitinib maleate

| Condition | 25° C./0% rH | 40° C./75% rH | 25° C./100% rH |
|---|---|---|---|
| Starting from | TMU solvate | TMU solvate | TMU solvate |
| Week 1 | TMU solvate | Form B | Form B |

TABLE 3-continued

Stability test results of tetramethyl urea solvate form of oclacitinib maleate

| Condition | 25° C./0% rH | 40° C./75% rH | 25° C./100% rH |
|---|---|---|---|
| Week 4 | TMU solvate | Form B | Form B |
| Week 12 | TMU solvate | Form B | Form B |

The stability tests of tetramethyl urea solvate form of oclacitinib maleate obtained by example 10 show that tetramethyl urea solvate form of oclacitinib maleate converses into oclacitinib maleate form B at conditions having a relatively high humidity (i.e. 40° C. at 75% rH and 25° C. at 100% rH). Whereas the tetramethyl urea solvate form of oclacitinib maleate obtained by example 10 is stable at a relatively low humidity (i.e. 25° C. at 0% rH).

Monohydrate Form of Oclacitinib Maleate

EXAMPLE 11

Monohydrate form of oclacitinib maleate was obtained by grinding 36 mg of oclacitinib base with 12 mg of maleic acid at RT for 15 min with a 'Fritsch Pulverisette 23 Mini-Mill' at a grinding frequency of 50 Hz. The resulting light yellow powder turned into an oily liquid, which then solidified after 2-3 days. The resulting solid was analysed by XRPD (FIG. 14A), DSC (FIG. 14B), TGA (FIG. 14B) and NMR (FIG. 14C). Peak listing of the XRPD results of FIG. 14A are provided in table 4 (peak listing between 3 and 30° 2θ).

TABLE 4

Peak listing FIG. 14A

| Name | 2θ | Relative Intensity |
|---|---|---|
| Peak #1 | 5.93° | 25.6% |
| Peak #2 | 6.98° | 6.7% |
| Peak #3 | 7.46° | 34.0% |
| Peak #4 | 9.51° | 18.3% |
| Peak #5 | 11.20° | 15.6% |
| Peak #6 | 11.90° | 28.7% |
| Peak #7 | 12.48° | 9.0% |
| Peak #8 | 12.67° | 6.8% |
| Peak #9 | 13.98° | 40.4% |
| Peak #10 | 14.97° | 17.1% |
| Peak #11 | 15.20° | 9.3% |
| Peak #12 | 16.32° | 3.1% |
| Peak #13 | 16.50° | 7.7% |
| Peak #14 | 16.77° | 1.7% |
| Peak #15 | 17.55° | 100.0% |
| Peak #16 | 17.90° | 8.1% |
| Peak #17 | 18.01° | 12.1% |
| Peak #18 | 18.33° | 27.8% |
| Peak #19 | 18.53° | 18.5% |
| Peak #20 | 18.75° | 5.0% |
| Peak #21 | 19.66° | 4.1% |
| Peak #22 | 20.19° | 1.8% |
| Peak #23 | 21.10° | 13.4% |
| Peak #24 | 22.21° | 6.6% |
| Peak #25 | 22.35° | 7.1% |
| Peak #26 | 22.55° | 32.9% |
| Peak #27 | 22.79° | 3.1% |
| Peak #28 | 23.30° | 17.6% |
| Peak #29 | 23.58° | 3.5% |
| Peak #30 | 23.92° | 7.5% |
| Peak #31 | 24.27° | 12.0% |
| Peak #32 | 25.10° | 1.6% |
| Peak #33 | 25.63° | 1.2% |
| Peak #34 | 25.97° | 4.3% |
| Peak #35 | 26.06° | 4.7% |
| Peak #36 | 26.38° | 4.9% |
| Peak #37 | 27.13° | 19.2% |

TABLE 4-continued

Peak listing FIG. 14A

| Name | 2θ | Relative Intensity |
|---|---|---|
| Peak #38 | 27.20° | 17.5% |
| Peak #39 | 27.40° | 20.4% |
| Peak #40 | 27.82° | 5.8% |
| Peak #41 | 28.05° | 14.8% |
| Peak #42 | 28.19° | 11.1% |

The DSC analysis was performed at a heating rate of 10 K/min. The thermogram (FIG. 14B) shows an endothermal peak at 81° C., followed by an exothermal event at 96° C. Subsequently a broad endothermal event occurs with two peaks at 118° C. and 133° C. Decomposition can be observed after about 150° C.

The TG analysis of oclacitinib maleate revealed a mass loss of 4% between 50 and 100° C. (FIG. 14B), which correlates with the presence of a monohydrate.

The 1H NMR analysis performed did not show any indication for the presence of additional impurities. The ratio of oclacitinib:maleic acid has been determined to be 1:1 (FIG. 14C).

EXAMPLE 12

Monohydrate form of oclacitinib maleate was obtained by dissolving 36 mg of oclacitinib base and 12 mg maleic acid in 1 mL of water at RT. The solution left for evaporation at RT overnight. The resulting suspension was then stirred for four days. The solid was then isolated by filtration and analysed by XRPD showing the presence of a crystalline substance in correspondence with the XRPD of FIG. 14A.

Stability Tests

The stability of monohydrate form of oclacitinib maleate obtained by examples 11 and 12 was tested at the three different conditions as defined above. The results of stability test are shown in table 5. In table 5, "monohydrate form of oclacitinib maleate" is abbreviated by "monohydrate".

TABLE 5

Stability test results of monohydrate form of oclacitinib maleate

| Condition | 25° C./0% rH | 40° C./75% rH | 25° C./100% rH |
|---|---|---|---|
| Starting from | Monohydrate | Monohydrate | Monohydrate |
| Week 1 | Monohydrate | Monohydrate | Monohydrate |
| Week 4 | Monohydrate | Monohydrate | Monohydrate |

The stability tests of monohydrate form of oclacitinib maleate obtained by examples 11 and 12 show that monohydrate form of oclacitinib maleate is stable under all storage conditions.

Oclacitinib Maleate Form B

EXAMPLE 13

Oclacitinib maleate form B was obtained by dissolving 36 mg oclacitinib base in 2 mL ethanol followed by the addition of a solution of 12 mg maleic acid in 1 mL of ethanol/water mixture and stirred at RT. After 20 minutes a suspension was formed. After the addition of 5 mL ethanol the suspension was allowed to stand overnight. The suspension was subsequently filtered and washed with ethanol at a temperature of about 0° C. The resulting white solid was analysed by XRPD (FIG. 15A), DSC (FIG. 15B), TGA (FIG. 15C) and NMR (FIG. 15D). Peak listing of the XRPD results of FIG. 15A are provided in table 6 (peak listing between 3 and 30° 2θ).

TABLE 6

Peak listing FIG. 15A

| Name | 2θ | Relative Intensity |
|---|---|---|
| Peak #1 | 6.25° | 14.98% |
| Peak #2 | 7.59° | 17.42% |
| Peak #3 | 8.95° | 26.21% |
| Peak #4 | 10.67° | 9.03% |
| Peak #5 | 12.54° | 1.97% |
| Peak #6 | 13.47° | 33.88% |
| Peak #7 | 13.47° | 33.88% |
| Peak #8 | 14.32° | 14.73% |
| Peak #9 | 15.23° | 100.00% |
| Peak #10 | 15.61° | 12.96% |
| Peak #11 | 15.89° | 2.63% |
| Peak #12 | 16.36° | 6.15% |
| Peak #13 | 16.54° | 21.58% |
| Peak #14 | 17.51° | 5.35% |
| Peak #15 | 17.68° | 12.48% |
| Peak #16 | 17.95° | 1.38% |
| Peak #17 | 18.49° | 0.83% |
| Peak #18 | 18.86° | 35.91% |
| Peak #19 | 19.05° | 6.65% |
| Peak #20 | 19.57° | 1.19% |
| Peak #21 | 19.97° | 1.11% |
| Peak #22 | 20.47° | 23.17% |
| Peak #23 | 20.65° | 6.15% |
| Peak #24 | 21.46° | 4.84% |
| Peak #25 | 21.60° | 1.66% |
| Peak #26 | 22.10° | 18.85% |
| Peak #27 | 22.68° | 21.56% |
| Peak #28 | 22.93° | 7.84% |
| Peak #29 | 24.12° | 11.91% |
| Peak #30 | 24.54° | 2.57% |
| Peak #31 | 25.25° | 12.56% |
| Peak #32 | 26.39° | 10.77% |
| Peak #33 | 26.56° | 3.35% |
| Peak #34 | 26.98° | 46.34% |
| Peak #35 | 27.16° | 22.05% |
| Peak #36 | 27.70° | 4.27% |
| Peak #37 | 28.19° | 10.87% |
| Peak #38 | 28.74° | 13.56% |
| Peak #39 | 28.81° | 4.92% |
| Peak #40 | 29.56° | 6.90% |
| Peak #41 | 29.78° | 2.30% |

The thermogram (FIG. 15B) shows a broad endothermal event between 40° C. and 80° C. and an endothermal peak at 145° C.

The TG analysis (FIG. 15C) of oclacitinib maleate revealed a mass loss of 5.29% between room temperature and 80° C. Decomposition can be observed after about.

The 1H NMR analysis performed did not show any indication for the presence of additional impurities.

Stability Tests

The stability of oclacitinib maleate form B obtained by example 13 was tested at the three different conditions as defined above. The results of stability test are shown in table 7.

TABLE 7

Stability test results of oclacitinib maleate form B

| Condition | 25° C./0% rH | 40° C./75% rH | 25° C./100% rH |
|---|---|---|---|
| Starting from | Form B | Form B | Form B |
| Week 1 | Form B | Form B | Form B |
| Week 4 | Form A | Form B | Form B |
| Week 12 | Form A | Form B | Form B |

The stability tests of oclacitinib maleate form B obtained by example 13 show that oclacitinib maleate form B converses into oclacitinib maleate form A at conditions having a relatively low humidity (i.e. 25° C. at 0% rH). The stability tests further show that oclacitinib maleate form B is stable at a relatively high humidity (i.e. 40° C. at 75% rH and 25° C. at 100% rH).

Solubility Tests

The thermodynamic solubility of different forms of oclacitinib maleate was tested by generating a saturated solution for each form (i.e. oclacitinib maleate form A, amorphous oclacitinib maleate and monohydrate form of oclacitinib maleate). After 15 minutes of stirring (600 rpm) and further 15 minute of an equilibrium phase the solution was filtrated over an 0.2 μm syringe filter into a vial with a known weight.

Figure 16:
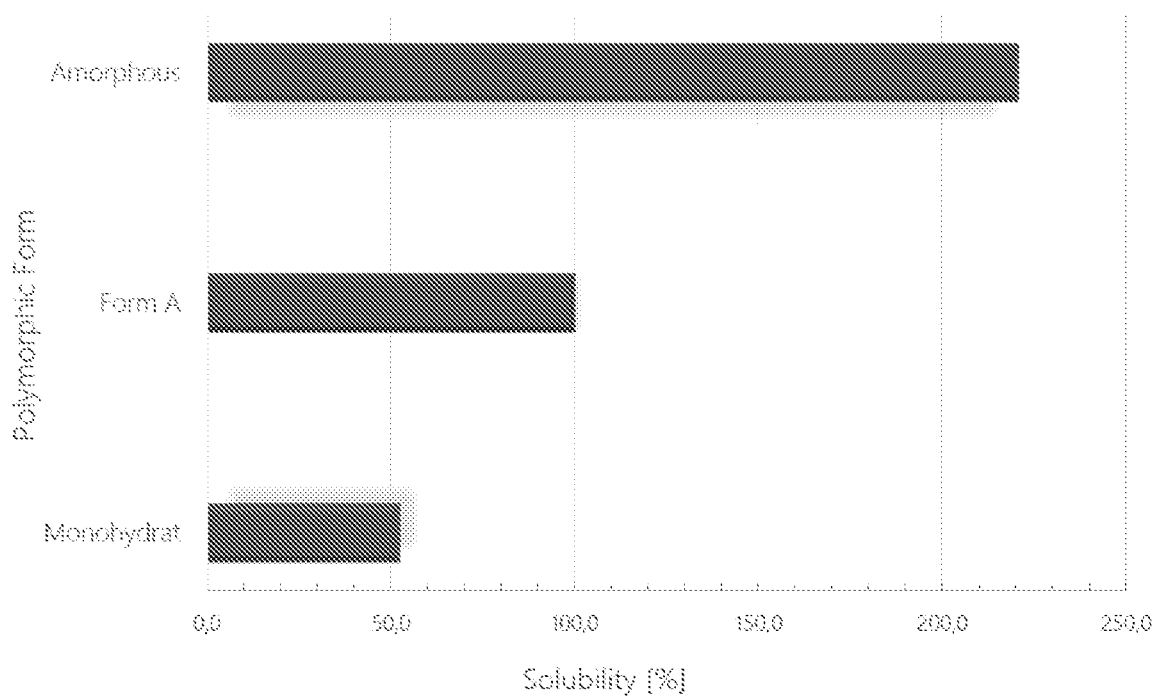
FIG. 16: shows the comparison of the thermodynamic solubility of oclacitinib maleate form A, amorphous oclacitinib maleate and monohydrate form of oclacitinib maleate.

Subsequently, the solvent was allowed to evaporate and the vial was then weighted again. The results are provided in table 8 below. Further, the results of the thermodynamic solubility tests are further shown in FIG. 16.

TABLE 8

Thermodynamic solubility test results

| Tested form | Used volume (mL) | Dissolved amount (mg) | Solubility (mg/mL) | Average (mg/mL) |
|---|---|---|---|---|
| Amorphous | 0.40 | 14.838 | 37.095 | 37.834 |
|  | 0.40 | 14.972 | 37.430 |  |
|  | 0.35 | 13.628 | 38.976 |  |
| Form A | 1.00 | 17.802 | 17.802 | 17.135 |
|  | 1.00 | 16.914 | 16.914 |  |
|  | 1.00 | 16.690 | 16.690 |  |
| Monohydrate | 2.00 | 18.106 | 9.053 | 8.994 |
|  | 2.00 | 18.094 | 9.047 |  |
|  | 2.00 | 17.768 | 8.884 |  |

Given the above results, and given the graphical comparison (FIG. 16) of the solubility of the different forms of oclacitinib maleate, wherein the solubility of oclacitinib maleate form A is normalized to 100%, it is noted that the amorphous form of oclacitinib maleate is more than twice as soluble compared to oclacitinib maleate form A. Whereas the solubility of monohydrate form of oclacitinib maleate is halved compared to oclacitinib maleate form A.

The invention claimed is:

1. A crystalline monohydrate form of oclacitinib maleate characterized by having an x-ray powder diffraction pattern comprising a characteristic peak at about 5.93±0.2° 2θ.

2. The crystalline monohydrate form of oclacitinib maleate according to claim 1, wherein the x-ray powder diffraction pattern comprises further characteristic peaks at about 11.90, 17.55, 22.55, and 27.40±0.2° 2θ.

3. The crystalline monohydrate form of oclacitinib maleate according to claim 1 characterized by having a DSC exhibiting an endothermic peak at about 81° C.

4. The crystalline monohydrate form of oclacitinib maleate according to claim 3, wherein the DSC further exhibits an exothermic peak at about 96° C. and an endothermic peak at about 118° C.

5. An oclacitinib maleate containing at least 50% of the oclacitinib maleate according to any of the preceding claims.

6. The oclacitinib maleate according to claim 5 for use in therapy.

7. The oclacitinib maleate according to claim 5 for use in treating:
  allergic reactions, allergic dermatitis, atopic dermatitis, eczema or pruritus in a mammal; and/or
  cancers, leukemia, lupus, multiple myeloma in a mammal.

8. The oclacitinib maleate for use according to claim 7, wherein the mammal comprises companion animals and/or livestock.

9. The oclacitinib maleate for use according to claim 8, wherein the mammal companion animals are dogs.

10. A method for preparing amorphous oclacitinib maleate comprising the steps of:
   a) providing a mixture of oclacitinib maleate and a stabiliser;
   b) dissolving oclacitinib maleate in a solvent to obtain a solution of oclacitinib maleate; and
   c) evaporating the solution of oclacitinib maleate obtained in step b), wherein the solvent comprises water and/or a water miscible solvent.

11. The method according to claim 10, wherein step b) and/or step c) are performed at a temperature of between 30° C. and 50° C.

12. The method according to claim 10, wherein step b) further comprises the step of, after obtaining the solution of oclacitinib maleate, filtering the obtained solution of oclacitinib maleate.

13. The method according to claim 10, wherein the water miscible solvent is selected from the group consisting of formamide, dimethyl sulfoxide, ethylene glycol, 1,3-propanediol, ethanol, acetone, pyridine, acetonitrile, methanol, tetramethyl urea, 1-pentanol, dichloromethane, tert-butanol, and combinations thereof.

14. The method according to claim 10, wherein the stabiliser is oclacitinib free base.

15. The method according to claim 10, wherein the prepared amorphous oclacitinib maleate is stable at a relative humidity of at most 30%.

* * * * *